(12) United States Patent
    Shenk et al.

(10) Patent No.: US 8,173,362 B2
(45) Date of Patent: *May 8, 2012

(54) CYTOMEGALOVIRUS SURFACE PROTEIN COMPLEX FOR USE IN VACCINES AND AS A DRUG TARGET

(75) Inventors: Thomas Shenk, Princeton, NJ (US); Dai Wang, Blue Bell, PA (US)

(73) Assignee: The Trustees of Princeton University, Princeton, NJ (US)

( * ) Notice: Subject to any disclaimer, the term of this patent is extended or adjusted under 35 U.S.C. 154(b) by 108 days.

This patent is subject to a terminal disclaimer.

(21) Appl. No.: 12/766,611

(22) Filed: Apr. 23, 2010

(65) Prior Publication Data

US 2011/0200633 A1    Aug. 18, 2011

Related U.S. Application Data

(62) Division of application No. 11/810,578, filed on Jun. 6, 2007, now Pat. No. 7,704,510.

(60) Provisional application No. 60/811,689, filed on Jun. 7, 2006, provisional application No. 60/902,544, filed on Feb. 20, 2007.

(51) Int. Cl.
    *C12Q 1/70*    (2006.01)
(52) U.S. Cl. ....... 435/5; 424/230.1; 424/424; 424/192.1
(58) Field of Classification Search .................. None
    See application file for complete search history.

(56) References Cited

U.S. PATENT DOCUMENTS

| 6,267,965 | B1 | 7/2001 | Paoletti et al. | |
| 7,704,510 | B2 * | 4/2010 | Shenk et al. | 424/230.1 |
| 2004/0110188 | A1 | 6/2004 | Hahn | |

FOREIGN PATENT DOCUMENTS

WO    WO-02066629 A2    8/2002

OTHER PUBLICATIONS

Akter et al., "Two Novel Spliced Genes in Human Cytomegalovirus," J. Gen. Viral. 84:1117-1122 (2003).
Borst, et al., Genetic Evidence of an Essential Role for Cytomegalovirus Small Capsid Protein in viral Growth, J. Viral. 75:1450-1458 (2001).
Britt, et al., Fields Virology, 3rd ed. 2493-2523 (1996).
Chee, et al., "Analysis of the Protein-Coding Content of the Sequence of Human Cytomegalovirus Strain Ad 169," Curr. Top. Microbiol. Immunol. 154:125-169 (1990).
Davison, et al., "The Human Cytomegalovirus Genome revisited: Comparison with the Chimpanzee Cytomegalovirus Genome," J. Gen. Virol. 84:17-28 (2003).
Elek, et al., "Development of a Vaccine Against Mental Retardation Caused by Cytomegalovirus Infection in Utero," Lancet 1:1-5 (1974).

Gerna, et al., "Dendritic-Cell Infection by Human Cytomegalovirus is Restricted to Strains Carrying Functional UL131-128 Genes and Mediates Efficient Viral antigen Presentation to CDB + T Cells," J. Gen. Virol. 86:275-284 (2005).
Gerna, et "Human Cytomegalovirus Replicates Abortively in Polymorphonuclear Leukocytes after Transfer from Infected Endothelial Cells via Transient Microfusion Events," J. Virol. 74:5629-38 (2002).
Grazia, et al., "In Vitro Selection of Human cytomegalovirus Variants Unable to Transfer Virus and Virus Products from Infected Cells to Polymorphonuclear Leukocytes and to grow in Endothelial Cells," J. Gen. Virol. 82:1429-1438 (2001).
Hahn, et al., "Human Cytomegalovirus UL131-128 Genes are Indispensable for Virus Growth in Endothelial Cells and Virus Transfer to Leukocytes," J. Virol. 78:10023-10033 (2004).
Hansen et al., "Complete Sequence and Genomic Analysis of Rhesus Cytomegalovirus," J. Virol. 77:6620-6636 (2003).
Hengel et al., "Driving Cells into Atheosclerotic Lesions—a Deleterious Role for Viral Chemokine Receptors?" Trends in Microbiol. 8:294-296 (2000).
Hobom, et al., "Fast Screening Procedures for Random Transposon Libraries of cloned Herpesvirus Genomes: Mutational Analysis of Human Cytomegalovirus Envelope Glycoprotein Genes," J. Virol. 74:7720-7729 (2000).
Huber, et al. "The Human Cytomegalovirus UL74 Gene Encodes the Third Component of the Glycoprotein H-Glycoprotein L-Containing Envelope Complex," J. Viral. 72:8191-8 197 1998.
Huber, et al., "Characterization of a Novel Third Member of the Human Cytomegalovirus glycoprotein H-Glycoprotein L Complex," J. Viral. 71:5391-5398 (1997).
Huber, et al., "Intracellular Formation and Processing of the Heterotrimeric gH-gL-gO (gCIII) Glycoprotein Envelope Complex of Human Cytomegalovirus," J. Viral. 73:3886-3892 1999.
Jarvis, et al., "Human cytomegalovirus Persistence and Latency in Endothelial Cells and Macrophages," Curr. Opin. Microbiol. 5:403-407 (2002).
Keay, et al., "Anti-Idiotype Antibodies that Mimic gp86 of Human Cytomegalovirus Inhibit Viral Fusion but Not Attachment," J. Virol. 65:5124-5128 (1991).
Kinzler, et al., "Characterization of Human Cytomegalovirus Glycoprotein-Induced Cell-Cell Fusion," J. Virol. 79:7827-7837 (2005).
Kohler, et al., "Continuous Cultures of Fused Cells Secreting Antibody of Predefined Specificity," Nature 256:495-497 (1975).
Kreitman, "Immunotoxins for Targeted Cancer Therapy," Adv. Drug Del. Rev., 31:53-88 (1998).
Leitner, et al., "DNA and RNa-Based Vaccines: Principles, Progress and Prospects," Vaccine 18:765-777 (2000).

(Continued)

*Primary Examiner* — Ali R. Salimi
(74) *Attorney, Agent, or Firm* — Marshall, Gerstein & Borun LLP

(57) ABSTRACT

Immunogenic compositions and prophylactic or therapeutic vaccines for use in protecting and treating against human cytomegalovirus (CMV) are disclosed. Subunit vaccines comprising a human CMV protein complex comprising pUL128 or pUL130, and nucleic acid vaccines comprising at least one nucleic acid encoding a CMV protein complex comprising pUL128 or pUL130 are described. Also disclosed are therapeutic antibodies reactive against a CMV protein complex comprising pUL128 or pUL130, as well as methods for screening compounds that inhibit CMV infection of epithelial and endothelial cells, methods for immunizing a subject against CMV infection, methods for determining the capability of neutralizing antibodies to inhibit CMV infection of cell types other than fibroblasts, and methods of diminishing an CMV infection.

12 Claims, 10 Drawing Sheets

OTHER PUBLICATIONS

Li et al., "Optimization of Humanized IgGs in Glycoengineered Pichia Pastoris," Nat. Biotech. 24:210-215 (2006).

Mach et al., "Complex formation by Human Cytomegalovirus Glycoproteins M (gpUL100) and N (gpUL73)," J. Virol 74:11881-92 (2000).

Marchini, et al., "Human Cytomegalovirus with IE-2 (UL122) Deleted Fails to Express Early Lytic Genes," J. Virol. 75:1870-1878 (2001).

Muller, "Determination of Affinity and Specificity of Anti-Hapten Antibodies by Competitive Radioimmunoassay," Meth. Enzymol. 92:589-601 (1983).

Murphy, et al., "Coding Potential of Laboratory and Clinical Strains of Human Cytomegalovirus," Proc. Natl. Acad. Sci. USA 100:14976-14981 (2003).

Nigro, et al., "Passive Immunization During Pregnancy for Congenital Cytomegalovirus Infection," N. Engl. J. Med. 353:1350-1362 (2005).

Patrone, et al., "Human Cytomegalovirus UL130 Protein Promotes Endothelial Cell Infection Through a Producer Cell Modification of the Virion," J. Virol. 79:8361-8373 (2005).

Plachter, et al., "Cell Types Involved in Replication and Distribution of Human Cytomegalovirus," Adv. Virus Res. 46:195-261 (1996).

Plotkin, et al., "Candidate Cytomegalovirus Strain for Human Vaccination," Infect. Immun. 12:521-527 (1975).

Rasmussen, et al., "Murine Monoclonal Antibody to a Single Protein Neutralizes the Infectivity of Human Cytornegalovirus," Proc. Natl. Acad. Sci. USA 81:876-880 (1984).

Rivailler, et al., "Genomic Sequence of Rhesus Cytomegalovirus 180.92: Insights into the Coding Potential of Rhesus Cytomegalovirus," J. Virol. 80:4179-4182 (2006).

Smith, et al., "Clinical Failure of CMV Retinitis with Intravitreal Cidofovir is Associated with Antiviral Resistance," Arch. Ophthalmol. 116:178-185 (1998).

Smith, et al., "Construction and Transposon Mutagenesis in *Eseherichia coli* of a Full-Length Infectious Clone of Psuedorabies Virus, an Alphaherpesvirus," J. Virol. 73:6405-6414 (1999).

Spear, et al., "Herpesvirus Entry an Update," J. Virol. 77:10179-10185 (2003).

Wang et al., PNAS, Dec. 2005, vol. 102. No. 50, pp. 18153-18158.

Wang, et al., "Human Cytomegalovirus Encodes a Highly Specific RANTES Decoy Receptor," Proc. Natl. Acad. Sci. USA 101:16642-166427 (2004).

Wang, et al., "Human Cytomegalovirus UL131 Open Reading Frame is Required for Epithelial Cell Tropism," J. Virol. 79:10330-10338 (2005).

Wang, et al., "Human Cytomegalovirus Virion Protein Complex Required for Epithelial and Endothelial Cell Tropism," Proceedings of the National Academy of Sciences of the United States of America, 102(50):18153-18158, XP002463457, ISSN:0027-8424, the whole document (2005).

Wang, et al., "Integrin $\alpha v\beta 3$ is a Coreceptor for Human Cytomegalovirus," Nat. Med. 11:515-521 (2005).

Yu, et al., "Construction of a Self-Excisable Bacterial Artificial Chromosome Containing the Human Cytomegalovirus Genome and Mutagenesis of the Diploid TRL/IRL 13 Gene," J. Virol 76:2316-2328 (2002).

* cited by examiner

```
                        SEQUENCE LISTING

<160> NUMBER OF SEQ ID NOS: 6

<210> SEQ ID NO 1
<211> LENGTH: 30
<212> TYPE: PRT
<213> ORGANISM: Human cytomegalovirus

<400> SEQUENCE: 1

Met Arg Leu Tyr Arg Val Trp Leu Ser Val Cys Leu Cys Ala Val Val
1               5                   10                  15

Leu Gly Gln Cys Gln Arg Glu Thr Ala Glu Lys Asn Asp Tyr
            20                  25                  30

<210> SEQ ID NO 2
<211> LENGTH: 30
<212> TYPE: PRT
<213> ORGANISM: Human cytomegalovirus

<400> SEQUENCE: 2

Met Arg Leu Cys Arg Val Trp Leu Ser Val Cys Leu Cys Ala Val Val
1               5                   10                  15

Leu Gly Gln Cys Gln Arg Glu Thr Ala Glu Lys Asn Asp Tyr
            20                  25                  30

<210> SEQ ID NO 3
<211> LENGTH: 30
<212> TYPE: PRT
<213> ORGANISM: Human cytomegalovirus

<400> SEQUENCE: 3

Met Arg Leu Cys Arg Val Trp Leu Ser Val Cys Leu Cys Ala Val Val
1               5                   10                  15

Leu Gly Gln Cys Gln Arg Glu Thr Ala Glu Lys Asn Asp Tyr
            20                  25                  30

<210> SEQ ID NO 4
<211> LENGTH: 30
<212> TYPE: PRT
<213> ORGANISM: Human cytomegalovirus

<400> SEQUENCE: 4
```

```
Met Gln Leu Cys Arg Val Trp Leu Ser Val Cys Leu Cys Ala Val Val
1               5                   10                  15

Leu Gly Gln Cys Gln Arg Glu Thr Ala Glu Lys Asn Asp Tyr
            20                  25                  30

<210> SEQ ID NO 5
<211> LENGTH: 30
<212> TYPE: PRT
<213> ORGANISM: Human cytomegalovirus

<400> SEQUENCE: 5

Met Arg Leu Cys Arg Val Trp Leu Ser Val Cys Leu Cys Ala Val Val
1               5                   10                  15

Leu Gly Gln Cys Gln Arg Glu Thr Ala Glu Lys Asn Asp Tyr
            20                  25                  30

<210> SEQ ID NO 6
<211> LENGTH: 30
<212> TYPE: PRT
<213> ORGANISM: Human cytomegalovirus

<400> SEQUENCE: 6

Met Arg Leu Tyr Arg Val Trp Leu Ser Val Cys Leu Cys Ala Val Val
1               5                   10                  15

Leu Gly Gln Cys Gln Arg Glu Thr Ala Glu Lys Asn Asp Tyr
            20                  25                  30
```

CYTOMEGALOVIRUS SURFACE PROTEIN COMPLEX FOR USE IN VACCINES AND AS A DRUG TARGET

RELATED APPLICATIONS

This application is a divisional of application Ser. No. 11/810,578, filed Jun. 6, 2007, now U.S. Pat. No. 7,704,510, which claims benefit of U.S. Provisional Application No. 60/811,689, filed Jun. 7, 2006, and U.S. Provisional Application No. 60/902,544, filed Feb. 20, 2007, the entire contents of each of which are incorporated by reference herein.

GOVERNMENT SUPPORT

Research leading to the disclosed inventions was funded, in part, with funds from the National Institute of Health, grant Nos: CA85786, CA82396, AI54430, and GM71508. Accordingly, the United States government may have certain rights in the inventions described herein.

FIELD OF THE INVENTION

The invention relates generally to the fields of vaccine development, passive immunity and antiviral drug discovery. More specifically, the invention relates to vaccines to cytomegalovirus, the development of antibodies as therapeutic agents for treatment of cytomegalovirus infections, and to screening assays for identification of molecules that inhibit cytomegalovirus infectivity.

BACKGROUND OF THE INVENTION

Various publications, including patents, published applications, technical articles and scholarly articles are cited throughout the specification. Each of these cited publications is incorporated by reference herein, in its entirety.

Cytomegalovirus (CMV) is a herpes virus classified as being a member of the beta subfamily of herpesviridae. According to the Centers for Disease Control and Prevention, CMV infection is found fairly ubiquitously in the human population, with an estimated 40-80% of the United States adult population infected. The virus is spread primarily through bodily fluids, and is frequently passed from pregnant mothers to the fetus or newborn. In most individuals, CMV infection is latent, although virus activation can result in high fever, chills, fatigue, headaches, nausea, and splenomegaly.

Although most human CMV infections are asymptomatic, CMV infections in immunocompromised individuals, such as newborns, HIV-positive patients, allogeneic transplant patients and cancer patients, can be particularly problematic. CMV infection in such individuals can cause severe morbidity, including pneumonia, hepatitis, encephalitis, colitis, uveitis, retinitis, blindness, and neuropathy, among other deleterious conditions. In addition, CMV is a leading cause of birth defects (Britt W J et al. 1996, Fields Virology, 3rd ed. 2493-2523). At present, there is no cure or preventive vaccine for CMV infection.

CMV infects various cells, including monocytes, macrophages, dendritic cells, neutrophils, endothelial cells, epithelial cells, fibroblasts, neurons, smooth muscle cells, hepatocytes, and stromal cells (Plachter B et al. 1996, Adv. Virus Res. 46:195-261). Infection of epithelial cells is significant because epithelial cells facilitate the spread of the virus within the host (Britt & Alford, 1996, supra). Infection of endothelial cells is significant because such cells are believed to be sites of human CMV persistence and latency, because endothelial cells are believed to be a gateway to leukocyte infection, because endothelial cells may facilitate mother to fetus/neonate transmission, and because infection of vascular endothelial cells is believed to contribute to various vascular pathologies, among other things (Jarvis M A et al. 2002, Curr. Opin. Microbiol. 5:403-7; Gerna G et al. 2002, J. Virol. 74:5629-38; Henget et al. 2000, Trends Microbiol. 8:294-6; and, Patrone M et al. 2005, J. Virol. 79:8361-73).

In immunocompromised individuals, CMV infects multiple organ systems, replicating in all major cell types. Although clinical isolates replicate in a variety of cell types, laboratory strains, such as AD169 (Elek, S. D. & Stern, H. 1974, Lancet 1, 1-5) and Towne (Plotkin, S. A., et al. 1975, Infect. Immun. 12, 521-527) replicate almost exclusively in fibroblasts (Hahn G et al. 2004, J. Virol. 78:10023-33). The restriction in tropism, which results from serial passage of the virus in fibroblasts, is a marker of attenuation (Gerna et al. 2002, supra). Mutations causing the loss of epithelial cell, endothelial cell, polymorphonuclear leukocyte, and dendritic cell tropism in human CMV laboratory strains have been mapped to three open reading frames (ORFs): UL128, UL130, and UL131 (Hahn et al. 2004, supra; Gema, G., et al. 2005, J. Gen. Virol. 86, 275-284). Mutation of any one of these ORFs in the FIX clinical isolate of human CMV blocked endothelial cell tropism (Hahn et al. 2004, supra).

CMV particles contain three major glycoprotein complexes, all of which are required for human CMV infectivity. The gCI complex includes two molecules of the UL55-coded gB. Each 160-kDa monomer is cleaved to generate a 116-kDa surface unit linked by disulfide bonds to a 55-kDa transmembrane component. Some antibodies immunospecific for gB inhibit the attachment of virions to cells, whereas others block the fusion of infected cells, suggesting that the protein might execute multiple functions at the start of infection. Several cellular membrane proteins interact with gB, and these interactions likely facilitate entry and activate cellular signaling pathways. The gCII complex contains the UL100-coded gM and UL73-coded gN, and it is the most abundant of the glycoprotein complexes. The complex binds to heparan sulfate proteoglycans, suggesting it might contribute to the initial interaction of the virion with the cell surface. It also could perform a structural role during virion assembly/envelopment, similar to the gM-gN complex found in some α-herpesviruses. The gCIII complex is comprised of UL75-coded gH, UL115-coded gL, and UL74-coded gO. All known herpesviruses encode gH-gL heterodimers (Spear, P. G. & Longnecker, R. 2003, J. Virol. 77, 10179-10185), which mediate fusion of the virion envelope with the cell membrane. Antibodies immunospecific for human CMV gH do not affect virus attachment but block penetration and cell-to-cell spread (Rasmussen, L. E. et al. 1984, Proc. Natl. Acad. Sci. USA 81, 876-880; Keay, S. & Baldwin, B. 1991, J. Virol. 65, 5124-5128). Expression of gH-gL in the absence of infection was sufficient to induce syncytia, and inclusion of gO in the assay did not enhance or block the fusion (Kinzler, E. R. & Compton, T. 2005, J. Virol. 79, 7827-7837). A gO-deficient mutant of AD169 shows a significant growth defect (Hobom, U. et al. 2000, J. Virol. 74, 7720-7729). Recently, it was reported that gH binds to integrin α vβ3 (Wang, X. et al. 2005, Nat. Med. 11, 515-521). However, the proteins encoded by UL131-UL128 heretofore have not been reported to be associated with any of the viral glyocoproteins.

There is a need for a CMV vaccine, and for effective means to control the spread and activation of the virus, particularly in immunocompromised individuals and pregnant women. There is also a need for methods to screen for antiviral compounds that inhibit cytomegalovirus infectivity.

SUMMARY OF THE INVENTION

One aspect of the invention features an immunogenic composition comprising a pharmaceutically acceptable carrier and a complex of cytomegalovirus (CMV) proteins comprising pUL128 or pUL130 and, optionally, at least one other virus or cellular constituent of a CMV virion complex. In various embodiments, the CMV proteins are from primate CMV, such as human, chimpanzee or rhesus monkey CMV.

In various embodiments, the other virus or cellular constituent of the virion complex can be one or more of pUL131, gH, gL, or gB. For instance, the complex can comprise pUL128 and pUL130, or it can comprise pUL128 alone or pUL130 alone. Or, the complex can comprise pUL128 and gH or gL, or pUL130 and gH or gL, or pUL128, pUL130 and gH or gL, or all four proteins. Alternatively, for instance, the complex can comprise pUL128, gH and gL or pUL30, gH and gL.

In one embodiment, multiple fragments of pUL128 are linked into one polypeptide chain. Alternatively, multiple fragments of pUL130 are linked into one polypeptide chain. In another embodiment, multiple fragments of pUL128 and pUL130 are linked into one polypeptide chain, or multiple fragments of pUL128, pUL130 and gH or gL are linked into one polypeptide chain. In yet another embodiment, multiple fragments of pUL128 and glycoprotein B are linked into one polypeptide chain, or multiple fragments of pUL130 and glycoprotein B are linked into one polypeptide chain. In another embodiment wherein multiple fragments of pUL128, pUL130 and glycoprotein B are linked into one polypeptide chain.

In this aspect of the invention, the complex can be produced by expression of one or more polynucleotides encoding the CMV proteins. For instance, the complex can be produced by expression of a CMV genome encoding an attenuated CMV, wherein the attenuation does not affect formation of the complex.

Another aspect of the invention features a subunit vaccine comprising a pharmaceutically acceptable carrier and at least one cytomegalovirus (CMV) protein or fragment thereof, selected from pUL128, pUL130, or a complex that includes pUL128 or pUL130, and, optionally, at least one other virus or cellular constituent of a CMV virion complex, wherein the vaccine induces an immune response against CMV in a recipient. In various embodiments, the CMV protein or fragment thereof is from primate CMV, such as a human, chimpanzee or rhesus monkey CMV. The subunit vaccine can further comprise an adjuvant.

In certain embodiments, at least one protein of the complex is coupled to a carrier protein. Suitable carrier proteins include, but are not limited to, albumin, ovalbumin, *Pseudomonas* exotoxin, tetanus toxin, ricin toxin, diphtheria toxin, cholera toxin, heat labile enterotoxin, keyhole lympet hemocyanin, epidermal growth factor, fibroblast growth factor, transferring, platelet-derived growth factor, poly-L-lysine, poly-L-glutamine, or mannose-6-phosphate.

In one embodiment, the protein, protein fragment or complex is expressed on the surface of an attenuated CMV virus particle. In another embodiment, the protein or fragment thereof is fused to one or more other proteins or fragments thereof present on the surface of the CMV virus particle. In another embodiment, the protein or fragment thereof is fused to at least one non-human CMV protein modified for expression on the surface of the human CMV virus particle.

Another aspect of the invention features a nucleic acid vaccine comprising a pharmaceutically acceptable carrier and a vector comprising at least one nucleic acid molecule encoding a CMV protein or fragment thereof, selected from pUL128, pUL130, or a complex that includes pUL128 or pUL130, wherein the at least one nucleic acid molecule is expressed in a vaccine recipient, and wherein the expression product induces an immune response against CMV in the recipient.

The nucleic acid vaccine can be constructed to express one or more proteins involved in the pUL128-pUL130-containing complex, and/or other virion proteins. In one embodiment, the CMV proteins are contained on anon-CMV vector. For instance, non-CMV vectors can express pUL128, or pUL130, or both pUL128 and pUL130. Or, non-CMV vectors can express pUL128, pUL130 and gH, gL or both gH and gL. In other embodiments, the nucleic acid vaccine can comprise a non-CMV vector that expresses one or more fragments of one or more of pUL128, pUL130, pUL131, gH, gL, or gB. In particular embodiments, two or more of such fragments are expressed on a single polypeptide.

Another aspect of the invention features antibodies or epitope-binding fragments thereof, which specifically bind to a virus-coded protein from a CMV virion complex that includes pUL128 or pUL130, wherein the antibodies or epitope-binding fragments thereof inhibit binding of the CMV virion complex to a cellular receptor, or CMV infection of a cell, or both. In various embodiments, the virion is from primate CMV, e.g., human, chimpanzee or rhesus monkey CMV.

The antibodies can be monoclonal antibodies or single-chain antibodies produced by recombinant DNA methods. In certain embodiments, they are human or humanized antibodies.

In certain embodiments, the antibodies specifically bind to pUL128. In one embodiment, the antibodies have equal or greater binding affinity for pUL128 than polyclonal antibody of antiserum having ATCC Accession No. PTA-8474. Exemplary antibodies of this type are polyclonal antibodies of antiserum having ATCC Accession No. PTA-8474. In another embodiment, the antibodies have equal or greater binding affinity for pUL128 than monoclonal antibodies produced by a hybridoma cell line having ATCC Accession No. PTA-8473. In another embodiment, the antibodies compete for binding to an epitope on pUL128 recognized by monoclonal antibodies produced by a hybridoma cell line having ATCC Accession No. PTA-8473. The antibodies can bind to the same epitope on pUL128 as do the monoclonal antibodies produced by the hybridoma cell line having ATCC Accession No. PTA-8473. Exemplary monoclonal antibodies of this type are monoclonal antibodies produced by a hybridoma cell line having ATCC Accession No. PTA-8473. Another embodiment features neutralizing binding partner of a CMV virion complex comprising pUL128, which comprises one or more virion binding sequences having 70% or greater identity to one or more complementarity determining regions (CDR) present in the monoclonal antibodies produced by a hybridoma cell line having ATCC Accession No. PTA-8473.

In certain embodiments, the antibodies specifically bind to pUL130. In one embodiment, the antibodies have equal or greater binding affinity for pUL130 than monoclonal antibodies produced by a hybridoma cell line having ATCC Accession No. PTA-8472. In another embodiment, the antibodies compete for binding to an epitope on pUL130 recognized by monoclonal antibodies produced by a hybridoma cell line having ATCC Accession No. PTA-8472. The antibodies can bind to the same epitope on pUL130 as do the monoclonal antibodies produced by the hybridoma cell line having ATCC Accession No. PTA-8472. Exemplary monoclonal antibodies of this type are monoclonal antibodies produced by a hybridoma cell line having ATCC Accession No. PTA-8472. Another embodiment features neutralizing binding partner of a CMV virion complex comprising pUL130, which comprises one or more virion binding sequences having 70% or greater identity to one or more complementarity determining regions (CDR) present in the monoclonal antibodies produced by a hybridoma cell line having ATCC Accession No. PTA-8472.

Any of the foregoing antibodies can further comprise glycosylation that has been modulated by expression in yeast cells that have been engineered to add glycan structures to proteins. Further, any of the foregoing antibodies can be formulated into a pharmaceutical composition.

In various embodiments, the foregoing antibodies are produced by exposing an immunocompetent subject to a CMV virion complex comprising pUL128 or pUL130 and at least one other virus or cellular constituent of the virion complex, wherein the antibodies are immunospecific for the CMV virion complex comprising pUL128 or pUL130, but are not immunospecific for any other CMV virion complex. Such antibodies can be polyclonal antibodies having components that bind to pUL128 or pUL130. In a particular embodiment, they are polyclonal antibodies having components that bind to pUL128 and components that bind to pUL130, wherein the antibodies are capable of binding at least twice as much pUL130 as pUL128.

Another aspect of the invention features a method of inhibiting CMV infection of endothelial or epithelial cells, comprising inhibiting binding of a CMV virion complex comprising pUL128 or pUL130 to the cells, thereby inhibiting the CMV infection. In one embodiment, binding inhibition is accomplished by treating the cells with an antibody immunospecific for the CMV virion complex, particularly for pUL128 or pUL130. The method can be practiced on cultured cells or in situ in cells within a living organism.

Another aspect of the invention features a method for screening compounds for the ability to inhibit entry of CMV into host cells, which comprises: (a) exposing host cells, in the presence or absence of a test compound, to one or more cellular receptors of host cells to CMV virions or a component thereof selected from (i) pUL128 or a fragment thereof, (ii) pUL130 or fragment thereof, or (iii) a complex that includes pUL128 or pUL130, and, optionally, at least one other virus or cellular constituent of a CMV virion complex; and (b) determining if the test compound interferes with binding of the CMV virions or component thereof to the host cells or cellular receptors, wherein the interfering of the binding is indicative that the test compound is capable of inhibiting the entry of the CMV into the host cells.

In certain embodiments of the method, the host cells are epithelial cells or endothelial cells. In one embodiment, the cellular receptors are disposed within a membrane fragment. The cellular receptors can be affixed to a solid support. In one embodiment, the CMV component is pUL128 or a fragment thereof, or pUL130 or a fragment thereof. The CMV component also can be affixed to a solid support. The CMV virions can be produced by expressing a virion encoding polynucleotide in cells transfected with a vector containing the polynucleotide. In an exemplary embodiment, the vector is BADrUL131. The test compound can be a biomolecule, organic chemical, inorganic chemical, or a fragment, analog, homolog, conjugate, or derivatives thereof.

In another embodiment, a selected test compound determined by the foregoing method to be capable of interfering with the binding of CMV or components thereof to the host cells or cellular receptors is subjected to a secondary screen comprising: (a) exposing the host cells to CMV virions in the presence or absence of the selected test compound; and (b) determining if the selected test compound inhibits one or more of (i) production of CMV proteins within the host cells; (ii) a cytopathic effect of CMV infection; or (iii) spread of virus proteins from cell to cell, the inhibition being further indicative that the test compound is capable of inhibiting the CMV infection.

Another aspect of the invention features a method of screening compounds for their ability to neutralize human CMV infectivity of endothelial or epithelial cells. The method comprises: (a) exposing the epithelial or endothelial cells to CMV virions comprising a virion complex that includes pUL128 or pUL130, in the presence or absence of a test compound; and (b) determining if the test compound inhibits entry of the CMV into the host cells, the inhibition being indicative that the test compound is able to neutralize human CMV infectivity of the endothelial or epithelial cells. In particular embodiments, the test compound is an antibody or epitope-binding fragment thereof, or a neutralizing binding partner of a CMV virion complex comprising pUL130 or pUL128. The CMV virions can be produced by expressing a virion encoding polynucleotide in cells transfected with a vector containing the polynucleotide. In one embodiment, the vector contains a genome of a clinical isolate of CMV. In another embodiment, the vector contains a genome of a laboratory strain of CMV that comprises, or that has been engineered to comprise a functional UL131-128 locus. In an exemplary embodiment, the vector is BADrUL131.

Another aspect of the invention features a method of immunizing a patient against CMV infection by administering to the patient an immunogenic composition comprising a pharmaceutically acceptable carrier and a complex of cytomegalovirus (CMV) proteins comprising pUL128 or pUL130 and, optionally, at least one other virus or cellular constituent of a CMV virion complex, under conditions permitting the patient to develop an immune response to the immunogenic composition.

Another aspect of the invention features a method of immunizing a patient against CMV infection by administering to the patient a subunit vaccine comprising a pharmaceutically acceptable carrier and at least one cytomegalovirus (CMV) protein or fragment thereof, selected from pUL128, pUL130, or a complex that includes pUL128 or pUL130, and, optionally, at least one other virus or cellular constituent of a CMV virion complex, under conditions permitting the patient to develop an immune response to the subunit vaccine.

Yet another aspect of the invention features a method of immunizing a patient against CMV infection by administering to the patient a nucleic acid vaccine comprising a pharmaceutically acceptable carrier and a vector comprising at least one nucleic acid molecule encoding a CMV protein or fragment thereof, selected from pUL128, pUL130, or a complex that includes pUL128 or pUL130, wherein the at least one nucleic acid molecule is expressed in the patient, under conditions permitting the patient to develop an immune response to the proteins encoded by the nucleic acid vaccine.

Still another aspect of the invention features a method of diminishing a CMV infection in a patient, comprising administering to the patient antibodies or epitope-binding fragments thereof, which specifically bind to a virus-coded protein in a CMV virion complex that includes pUL128 or pUL130, wherein the antibodies or epitope-binding fragments thereof inhibit binding of the human CMV virion complex to a cellular receptor, or CMV infection of a cell, or both, thereby diminishing the CMV infection in the patient.

Other features and advantages of the invention will be understood by reference to the drawings, detailed description and examples that follow.

DETAILED DESCRIPTION OF ILLUSTRATIVE EMBODIMENTS

Figure 1:
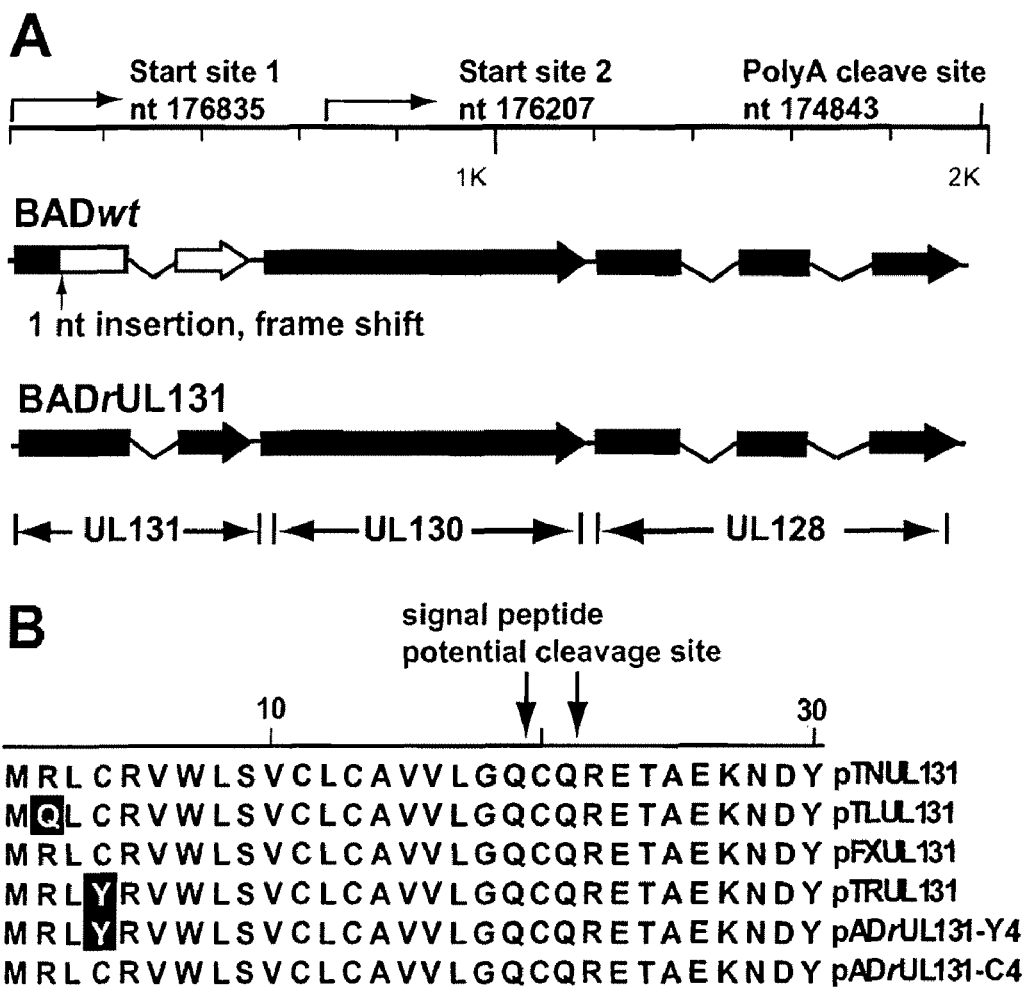
FIG. 1 shows the human CMV UL131-128 locus. (A) Diagram of the locus. The positions of transcriptional start sites and poly(A) cleavage sites are indicated. Solid boxes represent the sequence of wild-type ORFs. The location of the point mutation in the AD169 UL131 gene is indicated, and the portion of UL131 that is not expressed is designated by an open box. (B) Amino acid sequence of the N-terminal domain of UL131 in two repaired AD169 derivatives, BADrUL131-Y4 (SEQ ID NO:1) and BADrUL131-C4 (SEQ ID NO:2, and human CMV variant strains, pTNUL131 (SEQ ID NO:3), pTLUL131 (SEQ ID NO:4), pFXUL131 (SEQ ID NO:5), and pTRUL131 (SEQ ID NO:6). The likely signal peptide cleavage sites are indicated.

Various terms relating to the methods and other aspects of the present invention are used throughout the specification and claims. Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a cell" includes a combination of two or more cells, and the like.

"Antibody" or "immunoglobulin" is used broadly to refer to both antibody molecules and a variety of antibody-derived molecules and includes any member of a group of glycoproteins occurring in higher mammals that are major components of the immune system. The term "antibody" is used in the broadest sense and specifically covers monoclonal antibodies, polyclonal antibodies, antibody compositions with polyepitopic specificity, bispecific antibodies, diabodies, and single-chain molecules, as well as antibody fragments (e.g., Fab, F(ab')2, and Fv), so long as they exhibit the desired biological activity. An immunoglobulin molecule includes antigen binding domains, which each include the light chains and the end-terminal portion of the heavy chain, and the Fc region, which is necessary for a variety of functions, such as complement fixation. There are five classes of immunoglobulins wherein the primary structure of the heavy chain, in the Fc region, determines the immunoglobulin class. Specifically, the alpha, delta, epsilon, gamma, and mu chains correspond to IgA, IgD, IgE, IgG and IgM, respectively. Immunoglobulin and antibody are deemed to include all subclasses of alpha, delta, epsilon, gamma, and mu and also refer to any natural (e.g., IgA and IgM) or synthetic multimers of the four-chain immunoglobulin structure. Antibodies non-covalently, specifically, and reversibly bind an antigen. The antigen binding activity is found in the V (variable) region of the antibody whereas the complement fixing and Ig receptor binding activity is found in the C region. There are structural constraints on the amount of sequence variation allowed in the V region. In fact the variation is mostly restricted to three regions within the N-terminal domain of both the heavy (H) and light (L) chains. In the 3-dimensional structure these regions form loops at the surface of the antibody molecule and these provide the binding surface between antibody and antigen. Because these regions determine the 'fit' between antibody and antigen they are referred to as the "complementarity determining regions" or "CDRs".

A "monoclonal antibody" is an antibody obtained from a population of substantially homogeneous antibodies, i.e., the individual antibodies comprising the population are identical except for possible naturally occurring mutations that can be present in minor amounts. For example, monoclonal antibodies may be produced by a single clone of antibody-producing cells. Unlike polyclonal antibodies, monoclonal antibodies are monospecific (e.g., specific for a single epitope). The modifier "monoclonal" indicates the character of the antibody as being obtained from a substantially homogeneous population of antibodies, and is not to be construed as requiring production of the antibody by any particular method. Screening assays to determine binding specificity of an antibody are well known and routinely practiced in the art. For a comprehensive discussion of such assays, see Harlow et al. (Eds.), Antibodies A Laboratory Manual; Cold Spring Harbor Laboratory; Cold Spring Harbor, N.Y. (1988), Chapter 6.

The term "neutralizing antibody" refers to a form of antibody that interacts with an infectious agent, such as a virus, and reduces or inhibits its ability to infect host cells.

"Biomolecules" include proteins, polypeptides, nucleic acids, lipids, polysaccharides, monosaccharides, and all fragments, analogs, homologs, conjugates, and derivatives thereof.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of an mRNA molecule also consists of the nucleotide residues of the mRNA molecule which are matched with an anti-codon region of a transfer RNA molecule during translation of the mRNA molecule or which encode a stop codon. The coding region may thus include nucleotide residues corresponding to amino acid residues which are not present in the mature protein encoded by the mRNA molecule (e.g., amino acid residues in a protein export signal sequence).

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Effective amount" or "therapeutically effective amount" are used interchangeably herein, and refer to an amount of a compound, formulation, material, or composition, as described herein effective to achieve a particular biological result. Such results may include, but are not limited to, the inhibition of virus infection as determined by any means suitable in the art.

As used herein "endogenous" refers to any material from or produced inside an organism, cell, tissue or system. "Exogenous" refers to any material introduced from or produced outside an organism, cell, tissue or system.

The term "expression" as used herein is defined as the transcription and/or translation of a particular nucleotide sequence driven by its promoter.

As used herein, the term "fragment," as applied to a nucleic acid, refers to a subsequence of a larger nucleic acid. A "fragment" of a nucleic acid can be at least about 15 nucleotides in length; for example, at least about 50 nucleotides to about 100 nucleotides; at least about 100 to about 500 nucleotides, at least about 500 to about 1000 nucleotides, at least about 1000 nucleotides to about 1500 nucleotides; or about 1500 nucleotides to about 2500 nucleotides; or about 2500 nucleotides (and any integer value in between).

As used herein, the term "fragment," as applied to a protein or peptide, refers to a subsequence of a larger protein or peptide. A "fragment" of a protein or peptide can be at least about 10 amino acids in length (e.g., as for a single linear epitope); for example at least about 20 amino acids in length; at least about 50 amino acids in length; at least about 100 amino acids in length, at least about 200 amino acids in length, at least about 300 amino acids in length, and at least about 400 amino acids in length (and any integer value in between).

"Homologous, homology" or "identical, identity" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous. By way of example, the DNA sequences 3'ATTGCC5' and 3'TATGGC are 50% homologous.

As used herein, "immunization" or "vaccination" is intended for prophylactic or therapeutic immunization or vaccination. "Therapeutic vaccination" is meant for vaccination of a patient with CMV infection.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell. Unless it is particularly specified otherwise herein, the proteins, virion complexes, antibodies and other biological molecules forming the subject matter of the present invention are isolated, or can be isolated.

The terms "patient," "subject," "individual," and the like are used interchangeably herein, and refer to any animal, or cells thereof whether in vitro or in situ, that can be infected with CMV. In certain non-limiting embodiments, the patient, subject or individual is a human.

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning and amplification technology, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

"Pharmaceutically acceptable" refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability. "Pharmaceutically acceptable carrier" refers to a medium that does not interfere with the effectiveness of the biological activity of the active ingredient(s) and is not toxic to the host to which it is administered.

As used herein, "test compound" refers to any purified molecule, substantially purified molecule, molecules that are one or more components of a mixture of compounds, or a mixture of a compound with any other material that can be analyzed using the methods of the present invention. Test compounds can be organic or inorganic chemicals, or biomolecules, and all fragments, analogs, homologs, conjugates, and derivatives thereof. Biomolecules include proteins, polypeptides, nucleic acids, lipids, polysaccharides, and all fragments, analogs, homologs, conjugates, and derivatives thereof. Test compounds can be of natural or synthetic origin, and can be isolated or purified from their naturally occurring sources, or can be synthesized de novo. Test compounds can be defined in terms of structure or composition, or can be undefined. The compound can be an isolated product of unknown structure, a mixture of several known products, or an undefined composition comprising one or more compounds. Examples of undefined compositions include cell and tissue extracts, growth medium in which prokaryotic, eukaryotic, and archaebacterial cells have been cultured, fermentation broths, protein expression libraries, and the like.

The term "therapeutic" as used herein means a treatment and/or prophylaxis. A therapeutic effect is obtained by suppression, remission, or eradication of a disease state associated with CMV infection.

The term "treatment" as used within the context of the present invention is meant to include therapeutic treatment as well as prophylactic, or suppressive measures for the disease or disorder. Thus, for example, the term treatment includes the administration of an agent prior to or following the onset of a disease or disorder thereby preventing or removing all signs of the disease or disorder. As another example, administration of the agent after clinical manifestation of the disease to combat the symptoms of the disease comprises "treatment" of the disease. This includes for instance, prevention of CMV propagation to uninfected cells of an organism. The phrase "diminishing CMV infection" is sometimes used herein to refer to a treatment method that involves reducing the level of infection in a patient infected with CMV, as determined by means familiar to the clinician.

"Variant" as the term is used herein, is a nucleic acid sequence or a peptide sequence that differs in sequence from a reference nucleic acid sequence or peptide sequence respectively, but retains essential properties of the reference molecule. Changes in the sequence of a nucleic acid variant may not alter the amino acid sequence of a peptide encoded by the reference nucleic acid, or may result in amino acid substitutions, additions, deletions, fusions and truncations. Changes in the sequence of peptide variants are typically limited or conservative, so that the sequences of the reference peptide and the variant are closely similar overall and, in many regions, identical. A variant and reference peptide can differ in amino acid sequence by one or more substitutions, additions, deletions in any combination. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis.

A "vector" is a replicon, such as plasmids, phagemids, cosmids, baculoviruses, bacmids, bacterial artificial chromosomes (BACs), yeast artificial chromosomes (YACs), as well as other bacterial, yeast and viral vectors, to which another nucleic acid segment may be operably inserted so as to bring about the replication or expression of the segment. "Expression vector" refers to a vector comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

Cytomegalovirus replicates in many different cell types, including epithelial cells, endothelial cells, and fibroblasts. However, laboratory strains of the virus, many of which were developed as attenuated vaccine candidates by serial passage in fibroblasts, have lost the ability to infect epithelial and endothelial cells. Their growth is restricted primarily to fibroblasts, due to mutations in the UL131-UL128 locus, which is comprised of the UL131 (also referred to as UL131A by some investigators), UL130 and UL128 genes. Earlier work demonstrated that the UL131-UL128 locus is a primary determinant of human CMV endothelial cell host range, and it has been determined by the present inventors that a functional UL131-128 locus is required for epithelial cell tropism as well. However, the nature of this function was undetermined, and indeed it was speculated that one or more of the UL131-UL128 gene products was a secreted cytokine (Alder PC et al., 2003, J. Gen. Virol. 84, 1117-1122; Hahn et al., 2004, supra).

It has now been demonstrated in accordance with the present invention that two products of the UL131-UL128 locus, pUL130 and pUL128, form a complex with gH and gL, but not gO. The AD169 laboratory strain, which lacks a functional UL131 protein, produces virions containing only the gH-gL-gO complex. An epithelial and endothelial cell tropic AD169 variant in which the UL131 ORF has been repaired, termed BADrUL131, produces virions that carry both gH-gL-gO and gH-gL-pUL128-pUL130 complexes. Antibodies against pUL130 or pUL128 block infection of epithelial and endothelial cells by BADrUL131 and the fusion-inducing factor X (FIX) clinical human cytomegalovirus isolate but do not affect the efficiency with which fibroblasts are infected.

It has also been discovered in accordance with the present invention that the cell surface antigen CD46 is a receptor by which CMV gains entry into epithelial and endothelial cells. As described in greater detail herein, monoclonal antibody specific for CD46 was shown to block CMV infectivity into epithelial and endothelial cells in a concentration dependent manner. Accordingly, CD46 is a new cellular target for development of antiviral agents.

Thus, one aspect of the invention features immunogenic compositions and vaccines for the prevention or treatment of CMV infection, and methods of immunizing an individual using such compositions. Such vaccines target the interaction between CMV and its cellular receptors, particularly through the virion membrane complex that includes gH, gL, pUL128, pUL130, possibly among other virus or cell coded proteins. Another aspect of the invention features antibodies or antigen-binding components thereof that are immunospecific for epitopes presented by the pUL130-pUL128-containing complex, or that can otherwise prevent binding of CMV to CD46 or another cell surface receptor through the pUL130-pUL128-containing complex. Another aspect of the invention features a method of diminishing CMV infection by administering one or more of the aforementioned antibodies into a patient infected with CMV. Another aspect of the invention features an assay for antibodies that are able to neutralize CMV infection of cells other than fibroblasts, e.g., epithelial and endothelial cells. Another aspect of the inventions features methods for identifying antiviral compounds that target the interaction between the pUL130-pUL128-containing complex of CMV and its cellular receptor, CD46 or any other cell surface receptor with which the complex interacts.

Immunogenic Compositions and Vaccines, and Methods of Use:

One aspect of the invention features an immunogenic composition comprising a pharmaceutically acceptable carrier and a complex of cytomegalovirus (CMV) proteins comprising pUL128 or pUL130 and at least one other virus or cellular constituent of a virion complex that includes pUL128 or pUL130. In one embodiment, the virion complex comprises pUL128 or pUL130 alone. In another embodiment, the virion complex comprises pUL128 and pUL130. In another embodiment, the virion complex comprises glycoproteins gL and/or gH, or both. In another embodiment, the virion complex comprises pUL128, pUL130, gL and gH. In another embodiment, the virion complex comprises or is associated with pUL131. In yet another embodiment, fragments of the above-mentioned proteins are utilized, either as individual polypeptides or as fusion products.

Any CMV whose genome comprises a UL131-128 locus that is functional, or that can be made functional through genetic manipulation, is suitable for use as a source of the aforementioned virion complex or components thereof In one embodiment, the CMV is human CMV. In another embodiment, the CMV originates from another primate, including but not limited to chimpanzee (Davison, A J et al. 2003, J. Gen. Virol. 84: 17-28) and rhesus monkey (Hansen, S G et al. 2003, J. Virol. 77:6620-36; Rivailler, P et al. 2006, J. Virol. 80:4179-82). The immunogenic composition may comprise a virion complex with components all from the same CMV (e.g., all from human CMV), or the components may be selected from CMVs of different species (e.g., pUL128 from human CMV, pUL130 from chimpanzee CMV, and other such combinations).

The CMV virion complex or components thereof may be prepared in a variety of ways, in accordance with methods well known in the art. For instance, they may be isolated from the surfaces of virus particles and utilized together or separated into various components. In certain embodiments, the complex is produced by expression of one or more polynucleotides encoding the CMV proteins, fragments of these proteins, or fused molecules. In certain embodiments, in addition to CMV proteins and/or CMV protein fragments, fused molecules can include non-CMV proteins, non-CMV protein fragments, and/or synthetic fragments of amino-acid sequence, as would be appreciated by the skilled artisan.

Nucleic acid sequences encoding the pUL128 and pUL130 proteins are known in the art, and are provided, in whole or in part, in public databases such as those at the National Center for Biotechnology Information (NCBI). By way of example, and not of limitation, UL128 sequences are provided at GenBank Accession Nos. DQ208272-DQ208294, and UL130 sequences are provided at GenBank Accession Nos. DQ208254-208270, and DQ011966-DQ011969. The open reading frame of human CMV UL128 is about 506-526 nucleotides in length, and is preferably 516 nucleotides in length. The open reading frame encodes a protein of about 162 to about 182 amino acids in length. Preferred encoded sequences are 172 amino acids in length. The open reading frame of human CMV UL130 is about 635-655 nucleotides in length, and is preferably 645 nucleotides in length. The open reading frame encodes a protein of about 205 to about 225 amino acids in length. Preferred encoded sequences are 215 amino acids in length.

At least six strains of human CMV have been cloned as infectious bacterial artificial chromosomes (BAC) and sequenced (Murphy, E et al. 2003, Proc. Natl. Acad. Sci. USA 100: 14976-14981. The BAC sequences are available at GenBank Accession Nos. AC146999 (laboratory strain AD)69, from which the BADrUL131 variant described herein was made); AC 146851 (laboratory strain Towne); AC 146904 (clinical isolate PH); AC146905 (clinical-like isolate Toledo); AC146906 (clinical isolate TR); and AC146907 (clinical isolate FIX). At least two strains of human CMV have been sequenced without prior BAC cloning, and are available at GenBank Accession Nos. BK000394 (laboratory strain AD 169) and AY446894 (clinical isolate Merlin). The entire genome of a chimpanzee CMV strain is available at GenBank Accession No. AF480884. Utilizing the teachings of the present application, the skilled artisan would be able to use any of the aforementioned sequences, or any other publicly available CMV sequence to prepare the virions, pUL130 and/or pUL128-containing virion complexes or components thereof described herein.

Another aspect of the invention features a subunit vaccine for treating an individual against infection with CMV. The subunit vaccines comprise a pharmaceutically acceptable carrier and an immunogenic CMV protein or protein complex, such as the virion complex described above, that includes pUL128 and/or pUL130 or fragments of pUL128 and/or pUL130. In one embodiment, the CMV protein or protein complex comprises pUL28. In another embodiment, the CMV protein or protein complex comprises pUL130. In another embodiment, the CMV protein or protein complex comprises pUL130 and pUL128. In another embodiment, the CMV protein or protein complex comprises other virion complex components or virion-associated proteins, such as one or more of gL, gH or pUL131. These proteins, protein fragments, fused proteins, fused protein fragments and components may be prepared by methods well known in the art, as set forth above in the description of the immunogenic compositions. It will be understood by the skilled artisan that an effective vaccine need not comprise an entire pUL128/pUL130 virion complex as described above. It need only comprise elements of that complex effective to elicit an immune response in a recipient sufficient to protect the recipient from CMV infection upon exposure to CMV.

Any CMV whose genome comprises a UL131-128 locus that is functional, or that can be made functional through genetic manipulation, is suitable for use as a source of the aforementioned components of the subunit vaccine. In one embodiment, the CMV is human CMV. In another embodiment, the CMV originates from another primate, including but not limited to chimpanzee (Davison, A J et al. 2003, J. Gen. Virol. 84: 17-28) and rhesus monkey (Hansen, S G et al. 2003, J. Virol. 77:6620-36; Rivailler, P et al. 2006, J. Virol. 80:4179-82). The vaccine may comprise components all from the same CMV (e.g., all from human CMV), or the components may be selected from CMVs of different species (e.g., pUL128 from human CMV, pUL130 from chimpanzee CMV, and other such combinations).

The subunit vaccine can further comprise an adjuvant. Adjuvants can be any substance that enhances the immune response to the antigens in the vaccine. Non-limiting examples of adjuvants suitable for use in the present invention include Freund's adjuvant, incomplete Freund's adjuvant, saponin, surfactants such as hexadecylamine, octadecylamine, lysolecithin, demethyldioactadecyl ammonium bromide, N,N-dioctadecyl-N'-N-bis (2-hydroxyethylpropane diamine), methoxyhexa-decyl-glycerol, pluronic polyols, polyanions such as pyran, diethylaminoethyl (DEAE) dextran, dextran sulfate, polybrene, poly IC, polyacrylic acid, carbopol, ethylene maleic acid, aluminum hydroxide, and aluminum phosphate peptides, oil or hydrocarbon emulsions, and the like.

The protein or protein complex including pUL128 and/or pUL130 or fragments of pUL128 and/or pUL130 can be coupled to a carrier protein. It is within the skill in the art to select suitable carrier proteins to couple to the CMV protein complex. Non-limiting examples of suitable carrier proteins include albumin, ovalbumin, *Pseudomonas* exotoxin, tetanus toxin, ricin toxin, diphtheria toxin, cholera toxin, heat labile enterotoxin, keyhole lympet hemocyanin, epidermal growth factor, fibroblast growth factor, transferring, platelet-derived growth factor, poly-L-lysine, poly-L-glutamine, mannose-6-phosphate, as well as various cell surface and membrane proteins, and the like.

In some embodiments, the protein or protein complex including pUL128 and/or pUL130 or fragments of pUL128 and/or pUL130 is expressed on the surface of an attenuated CMV virus particle. Methods to attenuate viruses are known in the art. For example, serial passage in fibroblasts can be used to attenuate CMV. Repeated passaging of virally-infected host cells is carried out in vitro until sufficient attenuation of the virus is achieved. Passaging may be conducted under specific environmental conditions, such as modulated temperature, pH, humidity, in order to select for viruses with reduced infectivity or pathogenicity. Mutagenesis can also be employed. For example, CMV virions can be exposed to ultraviolet or ionizing radiation or chemical mutagens, according to techniques known in the art. Recombinant techniques can also be used to produce attenuated CMV virions. For example, site-directed mutagenesis, gene replacement, or gene knockout techniques can be used to derive virus strains with attenuated infectivity or pathogenicity. Preferably, attenuated CMV exhibit a diminished capacity for infectivity, and/or pathogenicity, yet remain capable of inducing an immune response that treats or protects the host against CMV infection. Examples of attenuated CMV strains include, but are not limited to, laboratory strains, such as AD169 and Towne, which replicate almost exclusively in fibroblasts. Such attenuated strains, engineered to produce a surface protein or protein complex including pUL128 and/or pUL130 or fragments of pUL128 and/or pUL130, could be grown in fibroblasts or other cell types, e.g., epithelial cells, for use as a vaccine.

In some embodiments, the pUL128 and/or pUL130 protein or protein complex, and derivatives thereof described herein may be administered as a component of a more complex vaccine that includes additional CMV gene products. These additional CMV gene products can be complete proteins and/or fragments of proteins. In one embodiment, immunogenic fragments of pUL128 and/or pUL130 may presented alone or may be combined into one polypeptide chain that includes immunogenic fragments of additional components of the pUL128-pUL130 virion complex, e.g., gH, and/or additional components of the virion, e.g., gB. Such polypeptides comprised of multiple immunogenic fragments may also contain non-CMV and/or synthetic amino acid sequences.

In some embodiments, the pUL128 and/or pUL130 protein or protein complex, and derivatives thereof described herein, can be administered as components of a vaccine vector. Vaccine vectors include modified viruses, bacteria and other microbes. For example, an adenovirus derivative can be produced that lacks one or more adenovirus genes or gene fragments and contains in its/their place nucleic acid encoding the pUL128 and/or pUL130 protein or protein complex, and derivatives thereof.

Vaccines can be formulated in aqueous solutions such as water or alcohol, or in physiologically compatible buffers such as Hanks' solution, Ringer's solution, or physiological saline buffer, including PBS. Vaccine formulations can also be prepared as solid form preparations which are intended to be converted, shortly before use, to liquid form preparations suitable for administration to a subject, for example, by constitution with a suitable vehicle, such as sterile water, saline solution, or alcohol, before use.

The vaccine compositions can also be formulated using sustained release vehicles or depot preparations. Such long acting formulations may be administered by implantation (for example subcutaneously or intramuscularly) or by intramuscular injection. Thus, for example, the vaccines may be formulated with suitable polymeric or hydrophobic materials (for example as an emulsion in an acceptable oil) or ion exchange resins, or as sparingly soluble derivatives, for example, as a sparingly soluble salt. Liposomes and emulsions can be used as delivery vehicles suitable for use with hydrophobic formulations. Sustained-release vehicles may, depending on their chemical nature, release the antigens over a range of several hours to several days to several weeks to several months.

The vaccine compositions may further include one or more antioxidants. Exemplary reducing agents include mercaptopropionyl glycine, N-acetylcysteine, β-mercaptoethylamine, glutathione, ascorbic acid and its salts, sulfite, or sodium metabisulfite, or similar species. In addition, antioxidants can also include natural antioxidants such as vitamin E, C, leutein, xanthine, beta carotene and minerals such as zinc and selenium.

Vaccine compositions may further incorporate additional substances to function as stabilizing agents, preservatives, buffers, wetting agents, emulsifying agents, dispersing agents, and monosaccharides, polysaccharides, and salts for varying the osmotic balance. The vaccines can further comprise immunostimulatory molecules to enhance vaccine efficacy. Such molecules can potentiate the immune response, can induce inflammation, and can be any lymphokine or cytokine. Nonlimiting examples of cytokines include interleukin (IL)-1, IL-2, IL-3, IL-4, 1L-12, IL-13, granulocyte-macrophage colony stimulating factor (GMCSF), macrophage inflammatory factor, and the like.

Subunit vaccines can be formulated for and administered by infusion or injection (intravenously, intraarterially, intramuscularly, intracutaneously, subcutaneously, intrathecally, intraduodenally, intraperitoneally, and the like). The vaccines can also be administered intranasally, vaginally, rectally, orally, topically, buccally, transmucosally, or transdermally.

An effective antigen dosage to treat against CMV infection can be determined empirically, by means that are well established in the art. The effective dose of the vaccine may depend on any number of variables, including without limitation, the size, height, weight, age, sex, overall health of the subject, the type of formulation, the mode or manner or administration, whether the virus is active or latent, whether the patient is suffering from secondary infections, or other related conditions.

Vaccine regimens can also be based on the above-described factors. Vaccination can occur at any time during the lifetime of the subject, including development of the fetus through adulthood. Supplemental administrations, or boosters, may be required for full protection. To determine whether adequate immune protection has been achieved, seroconversion and antibody titers can be monitored in the patient following vaccination.

The invention also features nucleic acid vaccines for treating against CMV infection. In general, nucleic acid vaccines, also referred to as genetic vaccines, utilize DNA or RNA encoding a antigen of interest, and rely on host expression of the genes to stimulate an immune response to the encoded polypeptide (Leitner W W et al. (2000) Vaccine 18:765-77). The nucleic acid vaccines of the present invention comprise a pharmaceutically acceptable carrier and at least one nucleic acid molecule encoding an immunogenic CMV protein or protein complex including pUL128 and/or pUL130 and possibly other virus and/or cell coded proteins, or fragments thereof that elicit an immune response. The nucleic acid molecule is expressed in host cells of the vaccine recipient, and the expression product induces an immune response to the CMV protein complex including pUL128 and/or pUL130. The immune response treats against CMV infection. Nucleic acid sequences encoding various CMVs and components thereof are known in the art, as described in detail above.

Nucleic acid vaccines can be formulated to target specific cells or cell types. For example, it may be preferred to target antigen presenting cells such as dendritic cells, monocytes, macrophages, B cells, and the like.

Antibodies and Methods of Use:

Also featured in the present invention are antibodies that specifically recognize epitopes within pUL128 or pUL130 or any constituent of the complex that includes pUL128 and pUL130 in the virus particle. These may include one or more of glycoprotein gH, glycoprotein gL or pUL131. In preferred embodiments, the antibodies inhibit CMV infection of a cell by blocking the ability of the virus to bind to receptors on the cell surface. Such antibodies are sometimes referred to herein as neutralizing antibodies, in accordance with the art-recognized definition.

Any antibody that specifically binds to pUL128 or pUL130 or to any constituent of the protein complex that includes these proteins in virions, can be used in the present invention. Any antibody that specifically binds to CD46 can also be used in the present invention. Monoclonal (single antibodies or mixtures of antibodies) and/or polyclonal antibodies can be used, from whatever source produced are preferred, although recombinant antibodies such as single chain antibodies and phage-displayed antibodies, and antigen binding fragments of antibodies such as the Fab or Fv can also be used. Antibodies that recognize pUL128, pUL130, any constituents of the CMV protein complex including pUL 128 and pUL130, and CD46, can be used in the invention. In one embodiment, the antibodies recognize epitopes of pUL128, pUL130, or other components of the virion complex as they are presented in the complex, but do not recognize pUL128 or pUL130, or other components of the virion complex in solution or otherwise apart from the virion complex. In another embodiment, the antibodies recognize epitopes of pUL128 or pUL130, or other components of the virion complex in solution or otherwise apart from the virion complex. Regardless of how the antibodies are produced, preferred embodiments of the invention utilize or are directed to neutralizing antibodies. Indeed, another aspect of the invention, set forth below, features an assay to identify desired neutralizing antibodies. Methods for raising and purifying antibodies are well known in the art. In addition, monoclonal antibodies can be prepared by any number of techniques that are known in the art, including the technique originally developed by Kohler and Milstein (1975) Nature 256:495-497.

Antibodies suitable for use in the methods of the invention include, for example, fully human antibodies, single chain antibodies, human antibody homologs, humanized antibody homologs, chimeric antibodies, chimeric antibody homologs, and monomers or dimers of antibody heavy or light chains or mixtures thereof. The antibodies of the invention can be intact immunoglobulins of any isotype, including types IgA, IgG, IgE, IgD, IgM (as well as all subtypes and idiotypes thereof). The light chains of the immunoglobulin may be kappa or lambda. The antibodies can be portions of intact antibodies that retain antigen-binding specificity, for example, Fab fragments, Fab' fragments, F(ab'), fragments, F(v) fragments, heavy chain monomers or dimers, light chain monomers or dimers, dimers consisting of one heavy and one light chain, and the like. Recombinant antibodies, including single chain antibodies and phage-displayed antibodies, diabodies, as well as individual antibody light chains, individual antibody heavy chains, chimeric fusions between antibody chains and other molecules, heavy chain monomers or dimers, light chain monomers or dimers, dimers consisting of one heavy and one light chain, and the like, can also be used.

The antibodies of the invention can be modified, e.g., by the covalent attachment of any type of molecule to the antibody such that covalent attachment does not prevent the antibody from binding to its epitope. Examples of suitable derivatives include, but are not limited to glycosylated antibodies and fragments, acetylated antibodies and fragments, pegylated antibodies and fragments, phosphorylated antibodies and fragments, and amidated antibodies and fragments. In one non-limiting example, functional attributes of the antibodies or fragments many be modulated by their production in yeast expressing human pathways that mediate the generation of antibodies with specific glycosylated structures (Li, H. et al., 2006, Nat. Biotech. 24:210-5). The antibodies and derivatives thereof of the invention may themselves be derivatized by known protecting/blocking groups, proteolytic—cleavage, linkage to a cellular ligand or other proteins, and the like. Further, the antibodies and derivatives thereof of the invention may contain one or more non-classical amino acids.

The antibodies of the invention can be variants having single or multiple amino acid substitutions, deletions, additions, or replacements that retain the biological properties (e.g., internalization, binding affinity or avidity, or immune effector activity) of the antibodies of the invention. The skilled artisan can produce variants having single or multiple amino acid substitutions, deletions, additions or replacements. These variants can include, among other things (a) variants in which one or more amino acid residues are substituted with conservative or nonconservative amino acids, (b) variants in which one or more amino acids are added to or deleted from the polypeptide, (c) variants in which one or more amino acids include a substituent group, and (d) variants in which the polypeptide is fused with another peptide or polypeptide such as a fusion partner, a protein tag or other chemical moiety, that may confer useful properties to the polypeptide, such as, for example, an epitope for an antibody, a polyhistidine sequence, a biotin moiety and the like.

Antibodies can be labeled/conjugated to various moieties, including detectable moieties and drugs/toxins. Drug/toxin moieties include, for example, bacterial toxins, viral toxins, organic chemicals, inorganic chemicals, radioisotopes, and the like. Antibodies can be labeled for use in biological assays (e.g., radioisotope labels, fluorescent labels) to aid in detection of the antibody. Antibodies may also be conjugated with toxins to provide an immunotoxin (see, Kreitman R J (1998). Adv. Drug Del. Rev., 31:53). Detectable moieties contemplated for use in the invention include, but are not limited to, radioisotopes, fluorescent dyes such as fluorescein, phyocoerythrin, Cy-3, Cy5, allophycocyanin, DAPI, Texas red, rhodamine, Oregon green, lucifer yellow, and the like, green fluorescent protein, red fluorescent protein, cyan fluorescent protein, yellow fluorescent protein, Cerianthus orange fluorescent protein, alkaline phosphatase, $\beta$-lactamase, chloramphenicol acetyltransferase, adenosine deaminase, aminoglycoside phosphotransferase (neo$^r$, G418$^r$) dihydrofolate reductase, hygromycin-B-phosphotransferase, thymidine kinase, lacZ (encoding $\alpha$-galactosidase), and xanthine guanine phosphoribosyltransferase, $\beta$-glucuronidase, placental alkaline phosphatase, secreted embryonic alkaline phosphatase, or firefly or bacterial luciferase. Enzyme tags are used with their cognate substrate. As with other standard procedures associated with the practice of the invention, skilled artisans will be aware of additional labels that can be used. In some embodiments, the antibody is conjugated to biotin, and subsequently contacted with avidin or strepatvidin having a detectable moiety tag.

As described in Example 2, murine monoclonal antibodies (mAbs) specific for pUL130 (3E3 and 3C5) and pUL128 (4B10), as well as rabbit anti-pUL128 polyclonal antibody (R551A), were generated by using GST fusion proteins as immunogens. Antiserum containing polyclonal antibody R551A, as well as hybridoma cell lines producing mAb 3E3 and 4B 10, respectively, were deposited with the patent depository of the American Type Culture Collection (ATCC) on Jun. 5, 2007 and given the following ATCC designations: ATCC Accession No. PTA-8474 for antiserum R551A; ATCC Accession No. PTA-8472 for the hybridoma producing mAB 3E3; and ATCC Accession No. PTA-8473 for mAb 4B10. These antibodies, or fragments thereof, may be used to practice the many aspects of the invention described herein.

Furthermore, it is well within the purview of the skilled artisan to obtain or design variants and/or derivatives of the deposited antibodies, e.g., through competitive binding assays or through genetic manipulation, which are able to bind pUL128 or pUL130, or complexes containing pUL128 or pUL130. Methods for determining antibody specificity and affinity by competitive inhibition can be found in Harlow, et al., Antibodies: A Laboratory Manual, 1988; supra; Colligan et al., eds., 1992, 1993, Current Protocols in Immunology, Greene Publishing Assoc. and Wiley Interscience, N.Y., and Muller, 1983, Meth. Enzymol. 92:589-601.

For instance, antibodies that compete for binding to an epitope on pUL128 or pUL130 recognized by the deposited mAbs, or antibodies that bind to the same epitope(s) as the deposited mAbs, are suitable for use in the present invention. In addition, a neutralizing binding partner of a CMV virion complex comprising pUL128 or pUL130, which comprises one or more complementarity determining regions (CDRs) having 70% or greater identity to a CDR present in the deposited mAbs, is also contemplated for use in the present invention. Preferably, the neutralizing binding partner has two or three CDRs with the requisite degree of identity. Preferably, the percent similarity in one or more of the CDRs is 75%, 80%, 85%, 90% 95% or more identical to one or more of the CDRs of the deposited mAbs. Methods of determining the sequence of antibody CDRs are well known to the skilled artisan, as are methods of designing such neutralizing binding partners.

Another aspect of the invention features a method of diminishing CMV infection by introducing antibodies that block binding of CMV through its pUL128-pUL130-containing complex to a host cell, e.g., through a cellular receptor, such as CD46, which is a target of the pUL128-pUL130-containing complex, in a CMV infected subject. In various embodiments, the antibodies are immunologically specific for one or more epitopes of constituents of the pUL130-pUL128-containing complex as presented when the proteins are associated as a complex on the surface of a virus particle or on a carrier protein or free in solution. In one embodiment, the antibodies are immunospecific for one or more epitopes of pUL130, while in another embodiment they are immunospecific for one or more epitopes of pUL128.

Assays:

The invention also features methods for screening compounds that inhibit the interaction between the CMV pUL130-pUL128-containing surface complex and cellular receptors or mediators of viral entry on the surfaces of host cells. In one embodiment, the screening assays involve contacting a CMV particle with a test compound, and contacting the test compound-treated CMV particle with CD46 or a cell or membrane fragment comprising CD46, and determining whether the test compound inhibits the CMV particle binding to CD46. Candidate compounds to be tested by the methods of the present invention include purified molecules, substantially purified molecules, molecules that are one or more components of a mixture of compounds, or a mixture of a compound with any other material. Test compounds can be organic or inorganic chemicals, or biomolecules, and all fragments, analogs, homologs, conjugates, and derivatives thereof. Test compounds can be of natural or synthetic origin, and can be isolated or purified from their naturally occurring sources, or can be synthesized de novo. Test compounds can be defined in terms of structure or composition, or can be undefined. The compound can be an isolated product of unknown structure, a mixture of several known products, or an undefined composition comprising one or more compounds. Examples of undefined compositions include cell and tissue extracts, growth medium in which prokaryotic, eukaryotic, and archaebacterial cells have been cultured, fermentation broths, protein expression libraries, and the like. In one embodiment of this invention, the test compound could be small peptides comprising amino acid sequences corresponding to constituents of the pUL128-pUL130-containing complex. The peptides can contain naturally occurring amino acids, chemically modified amino acids and/or synthetic derivatives of amino acids. In a preferred embodiment of this invention, the peptides can be 8-20 amino acid units in length.

In one embodiment, the screening assays comprise contacting a CMV protein or protein complex including pUL128 and/or pUL130 or a fragment of pUL128 and/or pUL130, with a test compound, and contacting the test compound-treated protein or protein complex with a host cell, cell membrane or membrane fraction comprising one or more cellular receptors to which the pUL128 and/or pUL130 complex binds, and determining whether the test compound inhibits the protein or protein complex binding to the cell or cell membrane. In another embodiment, the screening assays comprise first contacting the cell or membrane fraction with a test compound, and then contacting the cell or membrane fraction, with a CMV protein or protein complex including pUL128 and/or pUL130, and determining whether the test compound inhibits binding of the CMV protein or protein complex including LTL 128 and UL130 to the cell or membrane fraction.

In some embodiments, the host cell or membrane fraction comprising a receptor such as CD46, is immobilized on a solid support. In other preferred embodiments, the CMV protein or protein complex including pUL128 and/or pUL30 is immobilized on a solid support. Examples of suitable solid supports include, but are not limited to, glass, plastic, metal, latex, rubber, ceramic, polymers such as polypropylene, polyvinylidene difluoride, polyethylene, polystyrene, and polyacrylamide, dextran, cellulose, nitrocellulose, pvdf, nylon, amylase, and the like. A solid support can be flat, concave, or convex, spherical, cylindrical, and the like, and can be particles, beads, membranes, strands, precipitates, gels, sheets, containers, wells, capillaries, films, plates, slides, and the like. The solid support can be magnetic, or a column.

For the screening assays, host cells and cell membrane fractions, CMV, or the CMV protein or protein complex including UL128 and/or UTL130 can be obtained from any source suitable in the art and prepared according to art-recognized methods. For instance, the BADrUL131 strain exemplified herein produces virions comprising gH-gL-pUL130-pUL128 complex. As mentioned, CD46 can be purified or bound to a cell membrane or membrane fragment. Purified CD46, or subunits thereof, can be synthesized de novo, or obtained from any mammalian cell that naturally expresses CD46. Host cells can include endothelial cells and epithelial cells. Constituents of the pUL130-pUL128 complex can be purified from the CMV virion. Purified virus proteins or a fused pUL130-128 complex can also be produced from recombinant expression systems, such as bacterial, yeast, insect cell systems, and the like. Techniques of recombinant cloning and protein expression and purification are well established in the art.

In another embodiment, candidate antiviral compounds shown to affect binding of the pUL130-128-containing complex to a host cell, cell membrane or cellular receptor can be further evaluated for their ability to reduce infectivity. This can be accomplished in a variety of ways known in the art, for example, by plaque reduction assays as described in the Examples herein or by monitoring the expression of a de novo synthesized protein encoded from the viral genome. Candidate antiviral compounds can also be tested in assays designed to measure membrane fusion, preferably at both the level of virus-cell and cell-to-cell spread of infection. Induction of infection and cell-to-cell spread can be monitored in many ways, including observation of cytopathic effect or monitoring the spread of virus proteins or marker proteins incorporated into the viral genome by immunofluorescence.

Another aspect of the invention features a cell culture assay by which to identify and quantify the CMV neutralizing activity that has been generated after immunization with vaccine candidates. This neutralization assay can be used to monitor potential efficacy of a vaccine in preclinical animal models; this is useful because human CMV does not infect non-human animal models and it is not feasible to perform human CMV immunization-challenge experiments in animal models prior to human trials. This assay also can be used to provide a quantitative measure of a critical aspect of vaccine function during clinical trials, i.e., the generation of neutralizing antibodies. An important underpinning of this aspect of the invention is the use of cell types than can be infected only by human CMV containing a functional pUL128-pUL130-containing complex, e.g., epithelial cells. Normal, unmodified human fibroblasts, a cell commonly used for analysis of human CMV infectivity would be ineffective in this assay because pUL128-pUL130-containing virions do not infect fibroblasts well (see Examples herein). Those of ordinary skill in the art can implement an assay for neutralization of human CMV infectivity of the appropriate cells. As a non-limiting example, a defined amount of infectious human CMV which contains on its surface the pUL128-pUL130-containing complex is mixed with dilutions of animal or human serum or antibodies derived from serum, and then the mixture is added to monolayers of epithelial cells, such as ARPE-19 cells, and the entry of virus into the cells is monitored. Entry can be monitored by many methods, including the de novo expression of a viral gene product or marker gene incorporated into the viral genome or by plaque-reduction assay as described in the Examples herein. By comparing the number of cells infected by untreated virus to the number of cells infected by virus after exposure to serum sample, it is possible to calculate the reduction in infectivity, or neutralization, caused by antibodies in the samples.

The following examples are provided to describe the invention in more detail. They are intended to illustrate, not to limit, the invention.

EXAMPLE 1

Human Cytommalovirus UL131 ORF is Required for Epithelial Cell Tropism

This example describes a systematic investigation of human CMV infection of epithelial cells, using a panel of cultured cells that originated from different organs and tissues. It was determined that cultured epithelial cells can be efficiently infected by human CMV strains with a wild-type UL131-UL128 locus. The AD169 laboratory strain can efficiently infect both epithelial and endothelial cells when the mutation in its UL131 ORF is repaired.

Materials and Methods

Cells and viruses. Primary human foreskin fibroblasts (HFFs) at passage 10-15 were maintained in Dulbecco's minimal essential medium (DMEM) supplemented with 10% new born calf serum. Two types of endothelial cells, immortalized human umbilical vein endothelial cells (HUVECs) and lung macovascular endothelial cells (LMVECs), were obtained from private sources but are otherwise available or can be obtained. The endothelial cells were cultured in EGM-2 medium (Combrex, East Rutherford, N.J.). HeLa cells, primary human MRC-5 embryonic lung fibroblasts and ARPE-19 retinal pigmented epithelial cells were purchased from ATCC. Both MRC-5 cells and ARPE-19 cells were used at passage 24-30. The MRC-5 cells were cultured in DMEM medium supplemented with 10% fetal bovine medium, and ARPE-19 cells were propagated in DMEM/Ham's F12 (1:1) medium containing 10% of fetal bovine serum. SW480, HCT116, 111299, MCF-7, SK-N-SH, SK-N-AS, IMR-32 cells were propagated in DMEM supplemented with 10% fetal bovine serum.

A derivative of the AD169 strain of human CMV (Yu, D et al., 2002, J Virol 76: 2316-2328) with a GFP marker (BADwt) was used as the parental AD 169 virus. In this variant, the UL21.5 region of the virus was replaced with a marker cassette containing the GFP coding region under control of a SV40 promoter followed by an internal ribosome entry site and a puromycin resistance gene (Wang, D et al., 2004, Proc. Natl. Acad. Sci. USA 101: 16642-166427). To repair the AD 169 UL131 coding sequence, linear recombination (Borst, EMS et al., 2001, J. Virol. 75:1450-1458) was employed to substitute the human CMV sequence from base pair 176685 to 176794 (sequence numbers according to Chee, M S et al., 1990, Curr. Top. Microbiol. Immunol. 154: 125-169) with a marker cassette containing kanamycin-resistance and LacZ genes in an infectious BAC clone carrying the BADwt genome. This clone was then transformed into E. coli GS500, and allelic exchange was performed with a pGS284 (Smith, G A and L W Enquist, 1999, J. Virol. 73: 6405-6414) derivative carrying the UL131 ORF and flanking sequences from the human CMV clinical TR strain (Smith, I L et al., 1998, Arch. Ophthalmol. 116: 178-185). To determine the recombination sites between the BAC clone and the shuttle plasmid, the UL131-UL128 locus were sequenced. Two repaired UL131 BAC clones with different N terminal protein sequences were generated by allelic exchange (FIG. 1). The viruses recovered from the repaired BAC clones were designated BADrUL131-Y4 and BADrUL131-C4.

Wild-type virus stocks were prepared from BAC clones of human CMV laboratory strains and clinical isolates: Towne (BTNwt) (Marchini, A et al., 2001, J. Virol. 75: 1870-1878), Toledo (BLTwt) (Murphy, E et al., 2003, supra), VR1814-FIX (BFXwt) (Hahn G et al., 2004, supra) and TR (BTRwt) ((Murphy, E et al., 2003, supra). BTNwt lacks US1-US12, BLTwt lacks US2-US11, BFXwt lacks IRS 1-US6, and BTRwt lacks US2-US5 ((Murphy, E et al., 2003, supra) as a consequence of BAC cloning. Viruses were reconstituted by electroporation of BAC DNA into HFFs, together with a plasmid expressing the viral UL82-coded pp71 protein, which enhances the infectivity of human CMV DNA. Virus stocks were prepared in HFF cells, and the first passage of each virus preparation was used for cell tropism studies.

Assays for virus infection and replication. To monitor the efficiency of infection, epithelial cells, endothelial cells or fibroblasts were transferred into 12-well plates and incubated overnight to produce subconfluent cultures. Monolayers were washed once with serum-free RPMI-1640 and infected with virus diluted in the same medium at a multiplicity of 1 pfu/cell. During the adsorption period, the plates were first subjected to centrifugation at 25° C. for 30 min at 1,000×g, and then incubated at 37° C. for 1 h. The inoculum was removed and fresh medium containing the serum appropriate to the cell type was added. At 48 h after infection, cultures were fixed in 2% paraformaldehyde and permeabilized with 0.1% Triton-X 100, and infected cells were identified by GFP expression and IE1 by immunofluorescence using monoclonal antibody 1 B 10 and Alexa 546-conjugated secondary antibody. The nuclei of cells were stained with 4', 6-diamidino-2-phenylindole (DAPI). Total cell numbers were determined by the number of DAPI-stained nuclei, and efficiencies of infection were calculated as the percentage of GFP and IE1 expressing cells in the total cell populations.

For analysis of virus growth kinetics, cells were infected at a multiplicity of 0.01 or 1 pfu/cell with BADwt (laboratory strain parent) or BADrUL131 viruses (repaired UL 131 ORF), with the exception of HeLa cells, which were only infected at a multiplicity of infection of 1 pfu/cell because HeLa cell cultures could not be maintained for the extended period of time needed for analysis of a low multiplicity infection. At various times after infection, cell-free virus was collected by harvesting medium from infected cultures and cell-associated virus was collected by three freeze-thaw cycles of infected cells in medium three times. Virus titers were determined by $TCID_{50}$ assay on MRC-5 cells. In contrast to parental AD169, the UL131-repaired viruses induced syncytia and exhibited reduced plaque forming efficiencies. Therefore, to compare the growth of the mutants and their wild-type parent, we relied on GFP gene expression rather than cytopathic effect to identify the infected wells in our $TCID_{50}$ assays. The use of the GFP marker carried on the viruses significantly increased the sensitivity and accuracy of the assays.

Results

Construction and characterization of an AD169 variant with a repaired UL131 ORF. Two spliced transcripts with a common polyA addition site were shown to be generated by the UL131-UL128 locus (Akter P C et al., 2003, supra; Hahn G et al., 2004, supra), but their 5' ends were not localized. To further characterize the transcripts produced by this locus, we mapped the two start sites (FIG. 1A) by using 5'-RACE analysis, and we confirmed the result using RNase protection assays (data not shown). The 5' ends are located at sequence positions 176835, just upstream of UL131, and 176207, within UL130 (numbering according to Chee, M S et al., 1990, supra). The mRNA with the 5' end upstream of the UL131 coding region has the potential to encode polypeptides encoded by all three ORFs, whereas the RNA whose 5' end maps within UL130 has the potential to encode a portion of UL130 and UL128. This 5' mapping confirms that the one base-pair insertion present in the UL131 ORF of AD169 (FIG. 1A) is, indeed, present within an mRNA that has been mapped to this locus.

The frame-shifted UL131 ORF in AD169 was repaired by constructing derivatives of the laboratory strain (BADrUL131) in which the mutated UL131 ORF was replaced with a wild-type UL131 ORF derived from the human CMV TR clinical strain (FIG. 1A). Two different viruses with a repaired UL131 ORF were generated, due to recombination events at two different sites between the BAC clone and the shuttle plasmid. The sequences of the UL131 ORFs from the newly generated viruses were compared with UL131 ORFs from Towne, Toledo, FIX and TR strains (FIG. 1B). Except for amino-acid positions 2 and 4, the sequences of UL131 ORFs from different clinical human CMV strains are identical. The UL131 sequence of BADrUL131-Y4 derives entirely from the TR strain, while the BADrUL131-C4 sequence is identical to that of FIX and Toledo strains (FIG. 1B).

It was previously shown (Hahn et al., 2004, supra) that a UL131 deletion mutant of the clinical isolate FIX, a BAC-cloned derivative of VR1814 (Grazia Revello, M et al., 2001, J. Gen. Virol. 82:.1429-1438), is no longer able to replicate in endothelial cells. To confirm that endothelial cell tropism was restored by repairing the UL131 gene in AD 169, two endothelial cell lines, HUVECs and LMVECs, were infected at multiplicity of 1 pfu/cell, and the cultures were assayed 48 h later for expression of the GFP marker carried by the viruses. Very few (<1%) GFP-expressing HUVECs were seen in BADwt infected cultures; in contrast, GFP could be detected in almost all the HUVECs infected by both BADrUL 131 viruses, demonstrating that the repaired AD169 variants had reacquired the ability to infect endothelial cells. LMVECs were more efficiently infected by BADwt (12%), but the efficiency of infection was considerably greater for BADrUL131-Y4 (96%) and BADrUL131-C4 (98%). In contrast to the UL131-deficient parent, the repaired BADrUL131 viruses induced syncytia in infected cultures of both fibroblasts and endothelial cells.

To evaluate the growth characteristics of the repaired viruses, MRC-5 fibroblasts and HUVECs were infected with BADwt or BADrUL 131 variants, and the production of cell-free and cell-associated virus in single step growth or multi-step growth analysis was assayed. The repaired viruses grew more poorly than their AD 169 parent in fibroblasts, generating a 10 to 100-fold reduced yield of both cell-free and cell-associated virus. The reduced yields correlated with extensive cell-cell fusion induced by the repaired viruses, although it is not clear that cell fusion compromises the efficiency of virus replication in fibroblasts. In contrast to fibroblasts, the repaired viruses grew more efficiently in endothelial cells than their laboratory-strain parent, producing about 20-fold more cell-free and 300-fold more cell-associated virus.

Collectively, these data demonstrate that repair of the mutated UL131 gene in AD169 compromises virus replication in fibroblasts and facilitates growth in endothelial cells.

UL128-131 locus-dependent infection of epithelial cells. The importance of UL131 for human CMV replication in epithelial cells was evaluated by examining the susceptibility of a panel of epithelial cell lines to BADwt and BADrUL131-Y4. Susceptibility to infection was assayed by monitoring expression of the UL123-coded IE1 protein and expression of the GFP marker genes carried by the two viruses. The epithelial cell lines originated from a variety of tissues: retina (ARPE-19), cervix (HeLa), colon (SW480 and HCT116), lung (H1299) and breast (MCF-7). It was found that HeLa and MCF-7 cells could be efficiently infected by BADrUL131, and the infection was highly dependent on UL 131 since a very low incidence f infection was seen for the AD 169 parent, BADwt. Cell-cell fusion in the MCF-7 epithelial cells, but not in HeLa cell cultures, was seen after infection with BADrUL131-Y4. This also demonstrated that GFP expression can lead to an underestimate of the percentage of cells that are infected, because the human CMV UL123-coded IE1 protein was detected in a greater proportion of cells. Presumably this reflects differences in the activity of the SV40 early promoter, which controls the expression of GFP in these viruses, relative to the human CMV immediate-early promoter.

To quantify the relative susceptibilities of the epithelial cell lines, a calculation was made of the percentage of cells expressing GFP from the viral genome in different epithelial cell populations after infection at identical input multiplicities with the parental virus or repaired virus. A repaired UL131 ORF was absolutely required to infect ARPE-19, HeLa, SW480, HCT116 and MCF-7 epithelial cells. The repaired ORF was not essential, but dramatically enhanced the efficiency of infection, in H1299 cells. Fibroblasts and endothelial cells were included as controls. Although no detectable differences in susceptibility to infection with BADwt versus BADrUL131-Y4 were evident in MRC-5 or HFF fibroblasts, GFP expression in HUVEC and LMVEC endothelial cells was dramatically enhanced. Finally, several neuron-derived cell lines were tested. The SK-N-AS, SK-N-SH and IMR-32 neuroblastoma cell lines showed variable susceptibilities to infection, but GFP expression was not UL 131 gene dependent.

The production of infectious progeny by the BADrUL131 repaired viruses was examined in ARPE-19 cells. The epithelial cells were infected at a multiplicity of 0.01 or 1 pfu/cell and the production of cell-associated and cell-free virus was monitored by $TCID_{50}$ assay on fibroblasts. In epithelial cells, BADrUL131-Y4 and BADrUL131-C4 produced a ≧10-fold greater yield than in fibroblasts and an ~100-fold greater yield than in endothelial cells. Further, BADrUL131 induced extensive cell-cell fusion in epithelial cell cultures, as it did in fibroblasts and endothelial cells.

The replication of the two BADrUL131 repaired viruses also was monitored in HeLa cells, an epithelial tumor cell line. Infection of HeLa cells generated a yield of cell-free virus that was reduced by a factor of ~1000 in comparison to the yield from APRE-19 cells. It is noteworthy that 98% of HeLa cells and 77% of ARPE-19 cells expressed the GFP marker after infection at a multiplicity, determined by $TCID_{50}$ assay on fibroblasts, of 1 pfu/cell with BADrUL131-Y4. In spite of the higher efficiency with which the marker was expressed in HeLa cells, the yield of infectious progeny was greater in ARPE-19 cells. Apparently, there is a block to efficient replication of human CMV in HeLa cells, relative to the efficiency of replication in ARPE-19 cells, which occurs after the genome reaches the nucleus and expresses the marker gene. In contrast to ARPE-19 cells, HeLa cells fail to undergo fusion after infection with BADrUL131 viruses, although significant cytopathic effects with characteristic cell rounding can be detected as early as 24 h after infection. This might reflect a failure of the virus to efficiently advance to the late stage of the replication cycle. This would inhibit expression of the UL131 ORF, which is expressed during the late phase.

A mutation in UL131 is responsible for the inability of AD 169 to efficiently replicate in epithelial cells. To further elucidate the role of the UL131-128 locus in human CMV epithelial cell tropism, assays for infection by four additional human CMV strains, Towne, Toledo, FIX and TR, were performed. UL130 is mutated in Towne and UL128 is disrupted in Toledo, whereas FIX and TR contain wild-type UL128, 130 and 131 ORFs. All of the virus strains infected the MRC-5 fibroblasts and expressed their IE1 protein equally well, but only TR and FIX efficiently infected HUVEC endothelial or ARPE-19 and HeLa epithelial cells. This result demonstrates that the Towne and Toledo strains do not efficiently enter epithelial cells and express their IE1 genes, and raises the possibility that the defect might result from mutations in the UL130 and UL128 ORFs, as has been shown for replication in endothelial cells (Hahn et al., 2004, supra).

Finally, the yields of infectious progeny were determined after infection of ARPE-19 epithelial cells with the set of human CMV strains. The repaired AD169 strain, BADrUL131-Y4, produced the highest yield in epithelial cells ($1 \times 10^7$ pfu/ml). AD 169, Towne, and Toledo, each of which contain a defect in the UL131-128 locus, generated little infectious progeny (~$1.5 \times 10^1$ pfu/ml), consistent with their inability to efficiently express their IE 1 genes in the epithelial cells. FIX and TR, which contain wild-type UL 131-128 loci, generated intermediate yields ($7 \times 10^3$ and $3 \times 10^3$ pfu/ml, respectively).

EXAMPLE 2

Human Cytomegalovirus Virion Protein Complex is Required for Epithelial and Endothelial Cell Tropism This example sets forth evidence demonstrating that pUL128 and pUL130 form a complex with gH/gL that is incorporated into virions. The complex is required to infect endothelial and epithelial cells but not fibroblasts.

Materials and Methods

Cell Culture. Human MRC-5 embryonic lung fibroblasts (American Type Culture Collection) were cultured in DMEM supplemented with 10% FBS, and ARPE-19 retinal pigmented epithelial cells (ATCC) were cultured in DMEM/Ham's F-12 medium (1:1) supplemented with 10% FBS. Each cell types were used at passage 24-30.

Human umbilical vein endothelial cells (HUVEC) were obtained by collagenase digestion of umbilical veins grown on gelatin-coated plates in RPMI 1640 supplemented with 10% FBS, endothelial cell growth supplements (50 µg/ml, Biomedical Technologies, Stroughton, Mass.) and heparin (75 µg/ml), and used at passage 3-6. During virus adsorption, and after viral infection, HUVECs were maintained without endothelial growth supplements or heparin. Human foreskin fibroblasts were grown in DMEM supplemented with 10% newborn calf serum, and used at passage 10-15.

Virus Preparation. The AD169 strain of human CMV contains a frame-shift mutation in the LTL131 gene. BADwt was produced from a bacterial artificial chromosome (BAC) clone of AD 169. BADrUL131is a derivative of BADwt in which the UL131 mutation has been repaired such that the ORF is identical to that in the TR human CMV clinical isolate. BAD-dIUL131-128 is a derivative of BADwt that was constructed by replacing the UL131-UL128 locus (base pairs 174865-176806) with a marker cassette containing the kanamycin resistance gene and LacZ gene using linear recombination. The BAC-cloned derivative of the VR1814 clinical isolate of human CMV is termed FIX, and virus reconstituted from that clone was termed BFXwt. Virus was prepared by electroporation of BAC DNAs into fibroblasts, and the first passage of the virus was used in this study. Virions were partially purified by centrifugation through a sorbitol cushion for use as virus stocks.

Antibodies. Anti-gB 7-17, anti-gM IMP91-3/1, anti-gH 14-4b, and AP86 monoclonal antibodies were obtained as gifts from W. Britt (University of Alabama, Birmingham). Rabbit polyclonal anti-gO antibody was obtained as a gift from T. Compton (University of Wisconsin, Madison). Murine monoclonal antibodies specific for pUL130 (3E3 and 3C5) and pUL128 (4B10), as well as rabbit anti-pUL128 polyclonal antibody (R551A), were generated by using GST fusion proteins as immunogens.

Protein Analysis. For pulse-chase analysis, MRC-5 cells were held for 1 h in medium lacking methionine and cysteine beginning at 72 h post-infection at a multiplicity of three plaque-forming units per cell. 200 µCi/ml (1 Ci=37 GBq) of $^{35}$S Express Protein Labeling Mix (PerkinElmer) was added for 1 h, the radioactivity was removed, and cells were then maintained for 20 or 120 min in medium containing excess unlabeled methionine and cysteine and 10% FBS. Cells were harvested and lysed in RIPA buffer (50 mM Tris, pH 7.4/150 mM NaCl11 mM EDTA/1% Nonidet P-40/0.1% SDS/0.5% deoxycholate) containing protease inhibitor mixture (Roche Applied Science, Indianapolis).

Before immunoprecipitation, lysates were incubated with preimmune mouse or rabbit serum overnight at 4° C., and then precleared by using protein A Sepharose (Amersham Pharmacia Biosciences) or protein G-agarose (Roche Applied Science) to remove proteins that interact nonspecifically with the beads. Antibodies were added to the precleared lysates, incubated overnight at 4° C., and then protein A Sepharose or protein G-agarose was added for 4 h at 4° C.

Immune complexes were collected by centrifugation, washed with RIPA buffer, suspended in reducing sample buffer (50 mM Tris, pH 6.8/10% glycerol/2% SDS/1% 2-mercaptoethanol), boiled for 5 min, and proteins were separated by electrophoresis in SDS-containing polyacrylamide gels. The gM-gN complex was assayed by electrophoresis in urea-containing polyacrylamide gels.

For analysis of virion proteins, virions were separated from noninfectious particles by centrifugation through glycerol-tartrate gradients. The purified virions were boiled in reducing or nonreducing sample buffer, and proteins were analyzed by Western blotting.

Neutralization Assay. Anti-pUL130 monoclonal antibodies were purified by affinity chromatography on protein G-agarose. To purify rabbit anti-pUL128 polyclonal antibodies, antiserum was first passed through GST-conjugated Sepharose to deplete anti-GST antibodies that resulted from the use of a pUL128-GST fusion protein as immunogen. This step was followed by affinity purification with protein A Sepharose. Neutralization of BADrUL131 was quantified by plaque-reduction assay. Purified antibodies were diluted in DMEM supplemented with 5% complement inactivated FBS, and mixed with an equal volume of virus. Samples were incubated at room temperature for 1 h. After incubation, 300-82 1 aliquots (100 plaque-forming units) were used to infect cell monolayers. Following adsorption, the inoculum was removed, and cells were overlaid with medium containing 1% agarose. Foci of GFP-expressing cells were counted 2-3 weeks later. Neutralization of FIX virus was quantified by using a microneutralization assay.

Figure 2:
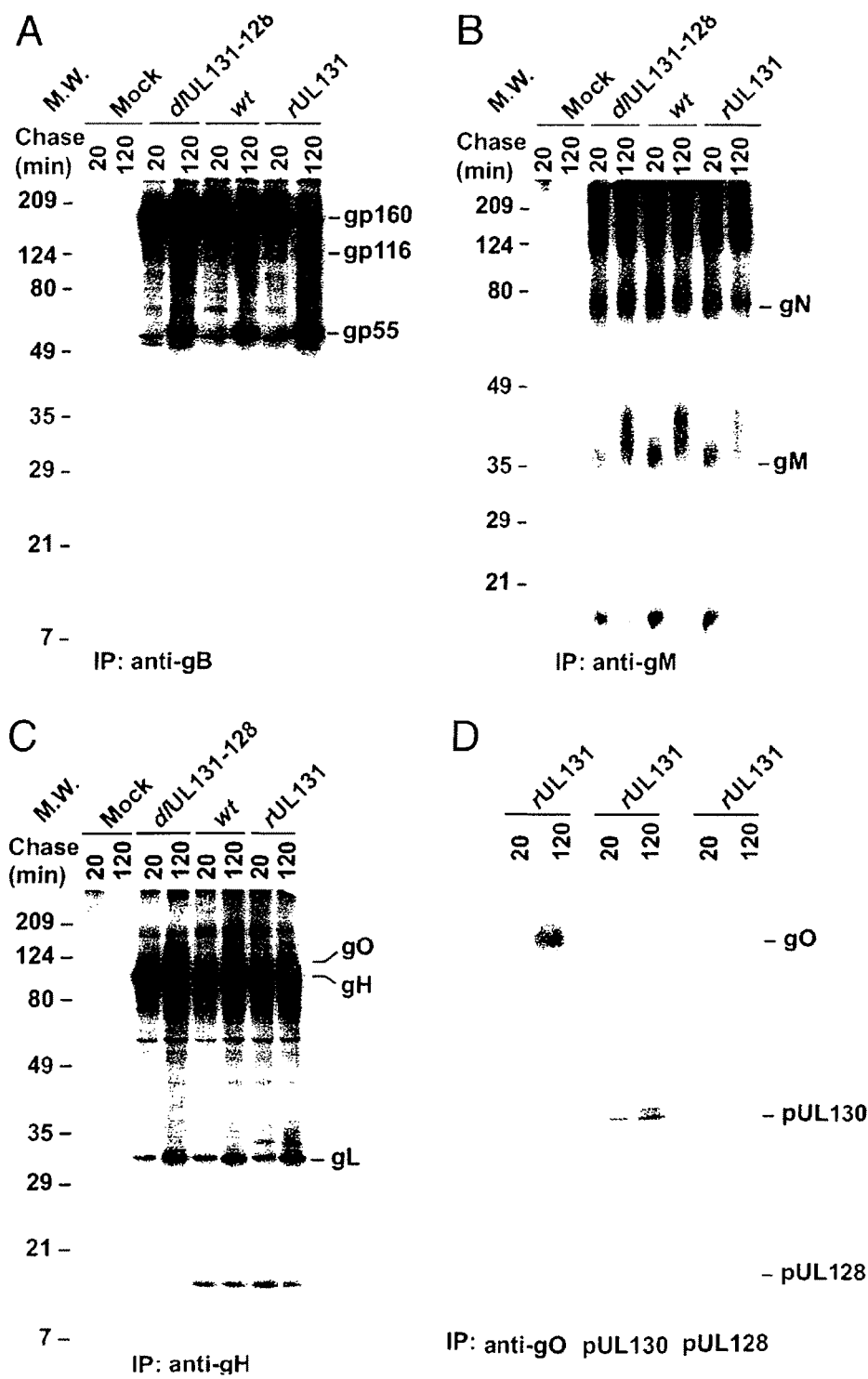
FIG. 2 shows that pUL128 and pUL130 form a complex with gH. MRC-5 cells were infected with BADdlUL131-128, BADva, or BADrUL131. Seventy-two hours after infection, cells were radiolabeled for 1 h, and chased for 20 or 120 min. Proteins were immunoprecipitated from cell lysates and analyzed by SDS PAGE, followed by autoradiography. Immunoprecipitations used anti-gB 7-17 (A), anti-gM IMP91-3/1 (B), anti-gH 14-4b (C), or anti-gH 14-4b, followed by anti-gO, anti-pUL130 3C5, or anti-pUL128 R551A (D). The positions at which marker proteins migrated are identified by their molecular weights (M.W.) in kilodaltons.

Results pUL128 and pUL130 are present in a complex with gH. To demonstrate that proteins encoded by the UL131-128 locus function in cooperation with one or more virus-coded fusogenic glycoproteins, virion glycoprotein complexes were searched for UL131-UL128-coded proteins. Fibroblasts were infected with three viruses: (1) BADwt, an isolate of the AD169 strain of human CMV with a nonfunctional UL131 ORF; (2) BADdlUL131-128, a derivative of BADwt that lacks the UL131-UL128 locus; and (3) BADrUL131, a derivative of BADwt with a repaired UL 131 ORF. At 72 h postinfection, cells were treated for 1 h with 35 5-labeled methionine and cysteine, the label was chased for 20 or 120 min, and then viral glycoprotein complexes were examined by immunoprecipitation (FIG. 2).

gB was found to be synthesized and glycosylated to produce a 160-kDa protein at 20 min postlabeling, and it was partially cleaved by 120 min to generate the mature gp55-gp 116 gB complex (FIG. 2A). The gM molecule was synthesized as a protein with an apparent molecular weight of 38 kDa, and it was modified 120 min after its synthesis to migrate as a diffuse 38- to 46-kDa band (FIG. 2B). The ~60-kDa protein that coprecipitated with gM was previously identified as gN (Mach M et al. (2000) J. Virol. 74:11881-92). No differences in gB or gM-gN were observed among the AD 169 variants.

Figure 3:
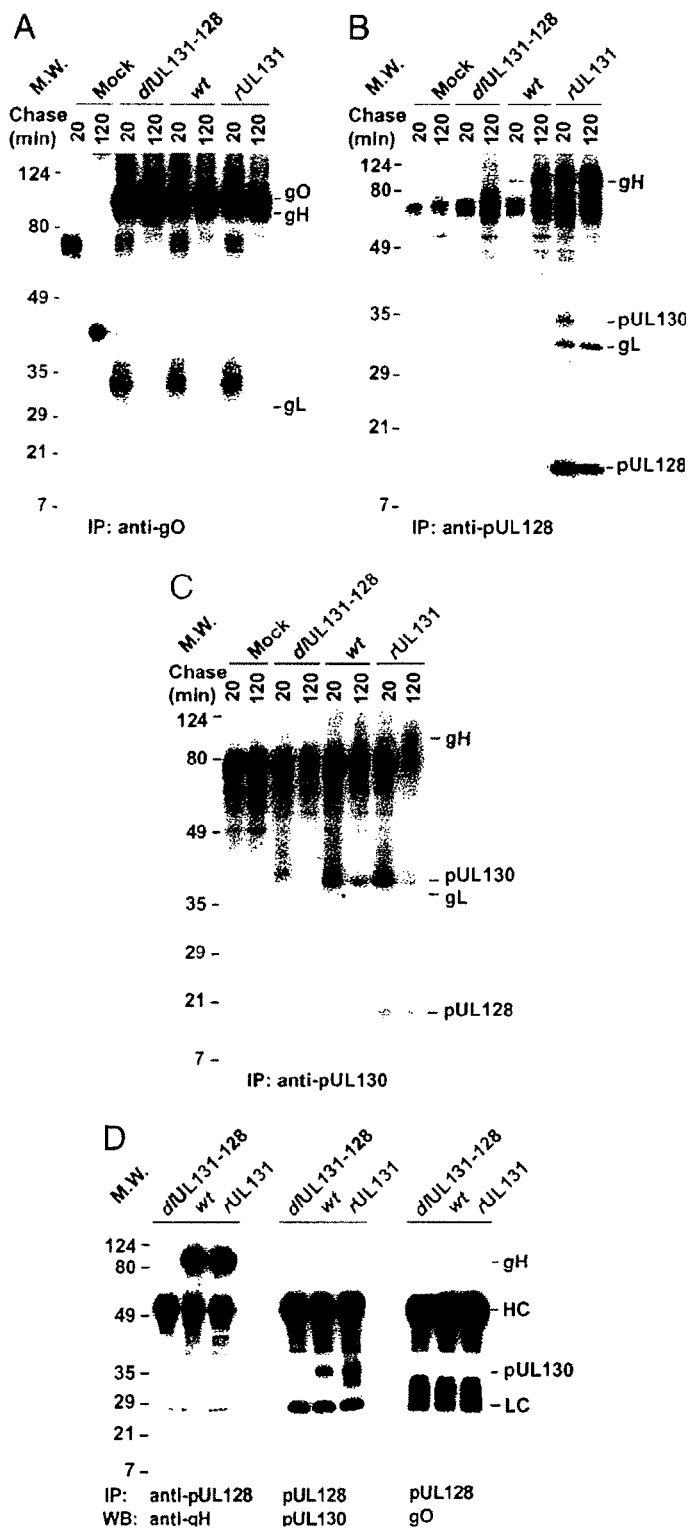
FIG. 3 shows that pUL128-pUL130 and gO form separate complexes with gH. MRC-5 cells were infected with BADdlUL131-128, BADwt, or BADrUL131. (A-C) Cells were radiolabeled for 1 h and chased for 20 or 120 min beginning at 72 h post infection. Proteins were immunoprecipitated from cell lysates and analyzed by SDS PAGE followed by autoradiography. Immunoprecipitations used anti-gO (A), anti-pUL128 4B10 (B), or anti-pUL130 3E3 (C). (D) Displays combined immunoprecipitation and Western blot assays of pUL128-interacting proteins. Cells were lysed at 72 h post infection, and extracts were subjected to immunoprecipitation with anti-pUL128 R551A antibody. The precipitated proteins were separated by SDS PAGE and analyzed by Western blotting with anti-gH AP86, anti-pUL130 3C3, or anti-gO antibodies. The positions at which marker proteins migrated are identified by their molecular weights (M.W.) in kilodaltons. Antibody heavy (HC) and light chains (LC) are designated.

In contrast, gH immunoprecipitates revealed distinct complexes after infection with the different viruses (FIG. 2C). gL and gO co-precipitated with gH from fibroblasts infected with all three viruses. In addition, a 16-kDa protein co-precipitated from extracts of BADwt- and BADrUL131-infected cells, but not from cells infected with BADdlUL131-128. Also, a 33-kDa protein (20 min) and a 33-plus 35-kDa doublet (120 min) were detected in the BADrUL131 gH coprecipitate. Based on the apparent sizes, it was surmised that the 16- and 33- to 35-kDa proteins were pUL128 and pUL130. To confirm this, sequential immunoprecipitation assays were performed. In the immunoprecipitation assays, the gH coprecipitating proteins from BADrUL131-infected lysates were reprecipitated with antipUL130 or -pUL128 antibodies (FIG. 2D, center and right panels). The 33- to 35- and 16-kDa proteins were specifically precipitated with these antibodies, confirming their identities as pUL130 and pUL128. Antibody to gH also coprecipitated gO from the BADrUL131 lysates (FIG. 2D, left panel).

pLTL128-pUL130 and gO form separate complexes with gH. To further characterize the gH interactions, coimmunoprecipitation experiments were performed using a gO-specific antibody (FIG. 3A). This antibody, like the gH antibody, captures the gH-gL-gO complex, and the three components were evident in the immunoprecipitates. Neither pUL128 nor pUL130 co-precipitated at a detectable level with the gO antibody, indicating that gO and pUL128-pUL130 form separate complexes with gH. Consistent with this, the pUL128-specific antibody precipitated gH, gL, and pUL130 from BADrUL131 lysates, but gO was not detected (FIG. 3B). In addition, anti-pUL130 antibody precipitated gH, gL, and pUL128- from BADrUL131-infected cell lysates, but not gO (FIG. 3C). The identities of gH and pUL 130 in the anti-pUL 128 immunoprecipitate were confirmed by Western blotting, although gO was not detected (FIG. 3D). These data indicate that pUL128-pUL130 and gO form separate complexes with gH.

pUL128 and pUL130 are present in virions. To test the possibility that the pUL128 and pUL130 complex is incorporated into virions, purified BADwt and BADrUL131 virions were assayed by Western blotting for gH, pUL128, and pUL130 (FIG. 4A). gH was found to be present in both virion preparations. BADrUL131, but not BADwt virions, were found to contain pUL130, consistent with the failure of pUL130 to interact with gH in a BADwt-infected cell lysate (FIG. 2C). Notably, pUL128 also was present only in BADrUL131 virions, even though it interacted with gH independently of pUL 130 and pUL 131 within extracts of BADwt-infected cells (FIG. 2C). These data indicate that only a complete gH-gL-pUL130-pUL128 complex is incorporated into virions.

Figure 4:
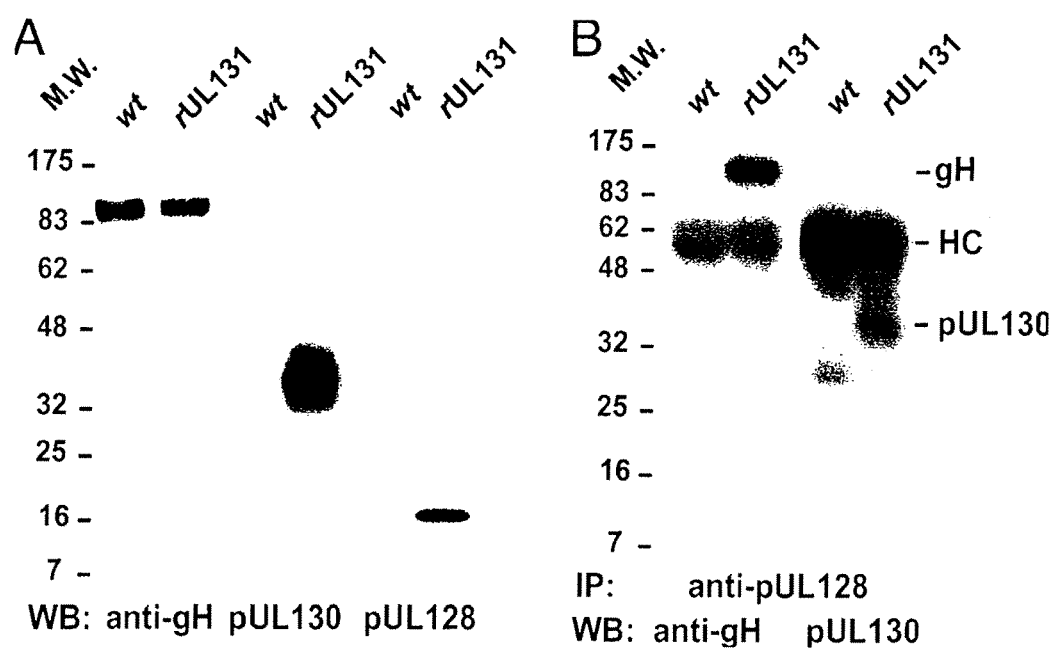
FIG. 4 shows that pUL128 and pUL130 are in virions. (A) BADwt and BADrUL131 virion proteins were analyzed by Western blotting using anti-gH AP86, anti-pUL130 3C5, or anti-pUL128 4B10 antibodies. (B) Virion proteins were immunoprecipitated with anti-pUL128 R551A and analyzed by Western blotting using anti-gH AP86 or anti-pUL130 3C5 antibodies. The positions at which marker proteins migrated are identified by their molecular weights (M.W.) in kilodaltons. Antibody heavy chains (HC) are designated.

To ascertain that pUL128 associates with gH in virions, BADrUL131 virion proteins were immunoprecipitated with pUL128-specific antibody and analyzed by Western blotting with anti-gH or -pUL130 antibodies (FIG. 4B). Both gH and pUL 130 proteins were captured with anti-pUL128 antibody, confirming that the three proteins are complexed in virions as in cell extracts.

Figure 5:
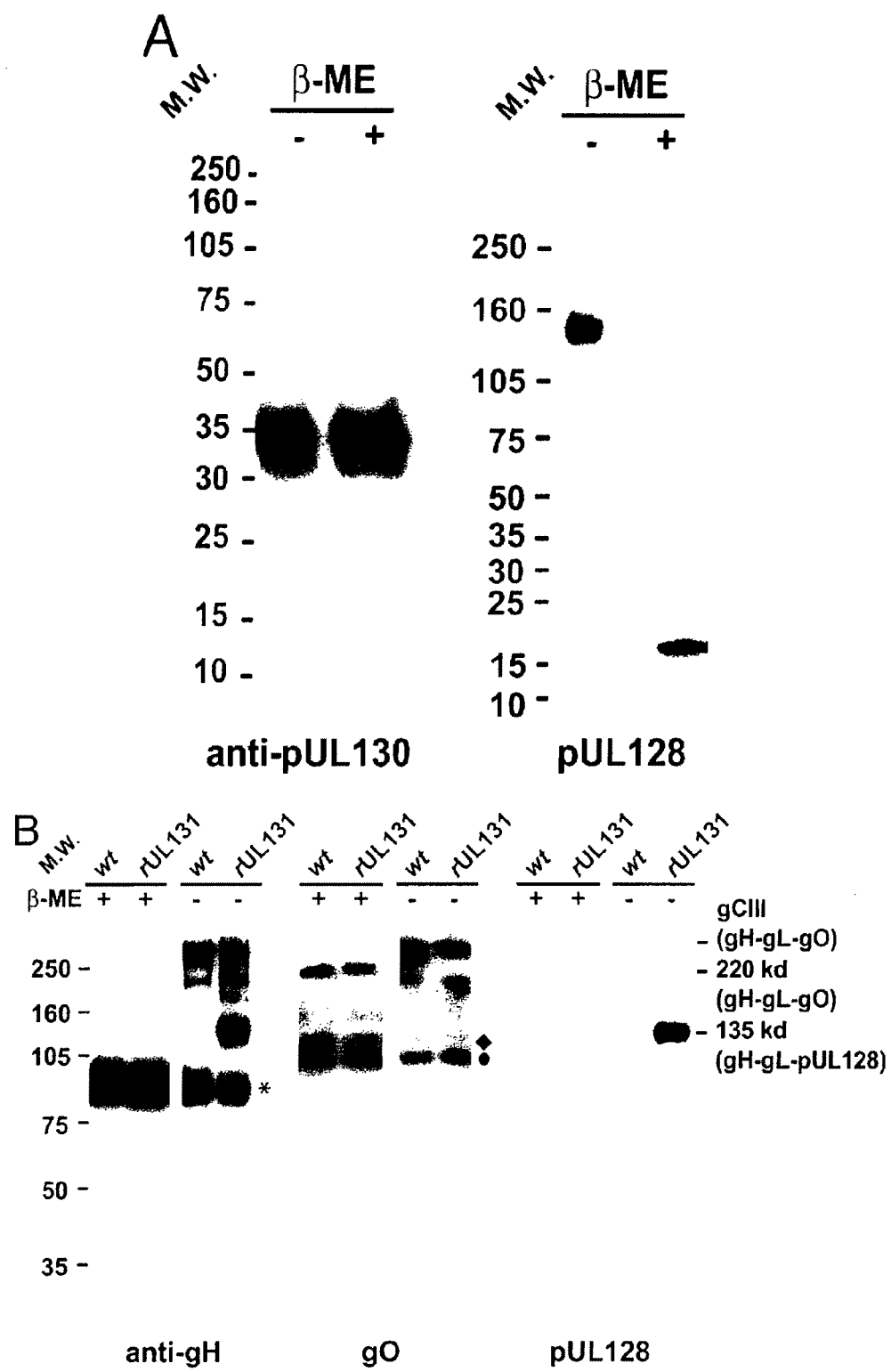
FIG. 5 shows the characterization of gH-gL complexes. (A) Disulfide linkage of pUL128 with gH-gL. Purified BADrUL131 proteins in buffer with or without 2-mercaptoethanol (β-ME) were subjected SDS PAGE 12% (left panel) or 4-20% (right panel), and analyzed by Western blotting using anti-pUL130 3C5 (left panel) or anti-pUL128 4B10 (right panel) antibodies. (B) Comparison of complexes in BADwt and BADrUL131 virions. Virion proteins were separated by reducing or nonreducing PAGE (8%), and analyzed by Western blotting using anti-gO (left pane)), anti-gH AP86 (center panel), or anti-pUL128 4B10 (Right) antibody. *=monomeric gli; The filled diamond and circle identify monomeric forms of gO. The positions at which marker proteins migrated are identified by their molecular weights (M.W.) in kilodaltons.

Characterization of gH complexes. Disulfide bonds link gH to gO and gL. Based on this observation, the possibility that gH interacts with pUL128 and pUL130 in the same manner was tested. BADrUL131 virion proteins were resolved by electrophoresis in reducing or nonreducing gels, transferred to membranes, and probed with anti-pUL130 or -pUL128 antibodies. As shown in FIG. 5A, left panel, the reducing agent did not change the mobility of pUL 130, suggesting that it is not linked to other proteins through disulfide bonds. In contrast, in the absence of 2-mercaptoethanol treatment, the anti-pUL128 antibody recognized a 135-kDa protein, and treatment with the reducing agent released monomeric pUL 128 (FIG. 5A, right panel). The complex presumably includes gH and gL in addition to pUL 128, because both gH and gL were precipitated from extracts of infected cells with pUL128-specific antibody (FIG. 3B). Its 135-kDa size is consistent with the interpretation that it contains one molecule each of gH (86 kDa), gL (31 kDa), and pUL128 (16 kDa).

Because pUL128 and gO form separate disulfide-bonded complexes with gH, the gH-gL-gO and gH-gL-pUL128 complexes present in BADwt versus BADrUL131 virions were compared. Under reducing conditions, (FIG. 5B, left panel, β2-mercaptoethanol), only monomeric, 86-kDa gH was observed. However, in the absence of reducing agent, more slowly migrating bands were evident (FIG. 5B, left panel, β2-mercaptoethanol), which presumably represented disulfide bonded complexes. In BADwt, major gH-containing complexes migrated at 300 and 220 kDa. The 220-kDa moiety is a partially modified gH-gL-gO complex, and the 300-kDa moiety corresponds to the mature gH-gL-gO (gCIII) complex (Huber M T et al. (1998) J. Virol. 72:8191-7; Huber M T et al. (1999) J. Virol. 73:3886-92; and, Huber M T et al. (1997) J. Virol. 71:5391-8). An additional gH-containing complex was present in BADrUL131, but not BADwt virions. The complex migrated with an apparent molecular weight of 135 kDa, the same mobility as the complex recognized by antibody to pUL128 (FIG. 5A), suggesting that it might be a gH-gL-pUL128 complex. Monomeric gH was observed in the absence of reducing agent in virions, indicating that a portion of it is not covalently bonded to other glycoproteins.

Additional Western blots were carried out on the same set of virion samples. gO-specific antibodies were observed to recognize the 300- and 220-kDa complexes, but not the 135-kDa complex (FIG. 5B, center panel). In contrast, the anti-pUL128 antibodies reacted with the 135-kDa moiety but not the larger complexes (FIG. 5B, right panel). These data indicate that two gH complexes are in BADrUL131 virions: gH-gL-pUL128-pUL130 and gH-gL-gO. BADwt virions contain only one gH complex, gH-gL-gO.

pUL128 and pUL130 antibodies block infection of epithelial and endothelial cells. BADrUL131 virions, which contain the gHgL-pUL128-pUL130 complex, can efficiently infect endothelial cells, epithelial cells, and fibroblasts (Wang D et al. (2005) J. Virol. 79:10330-8). BADwt, which lacks the complex, is restricted to fibroblasts. As such, neutralization assays were carried out to determine whether this complex is required to infect epithelial or endothelial cells.

Figure 6:
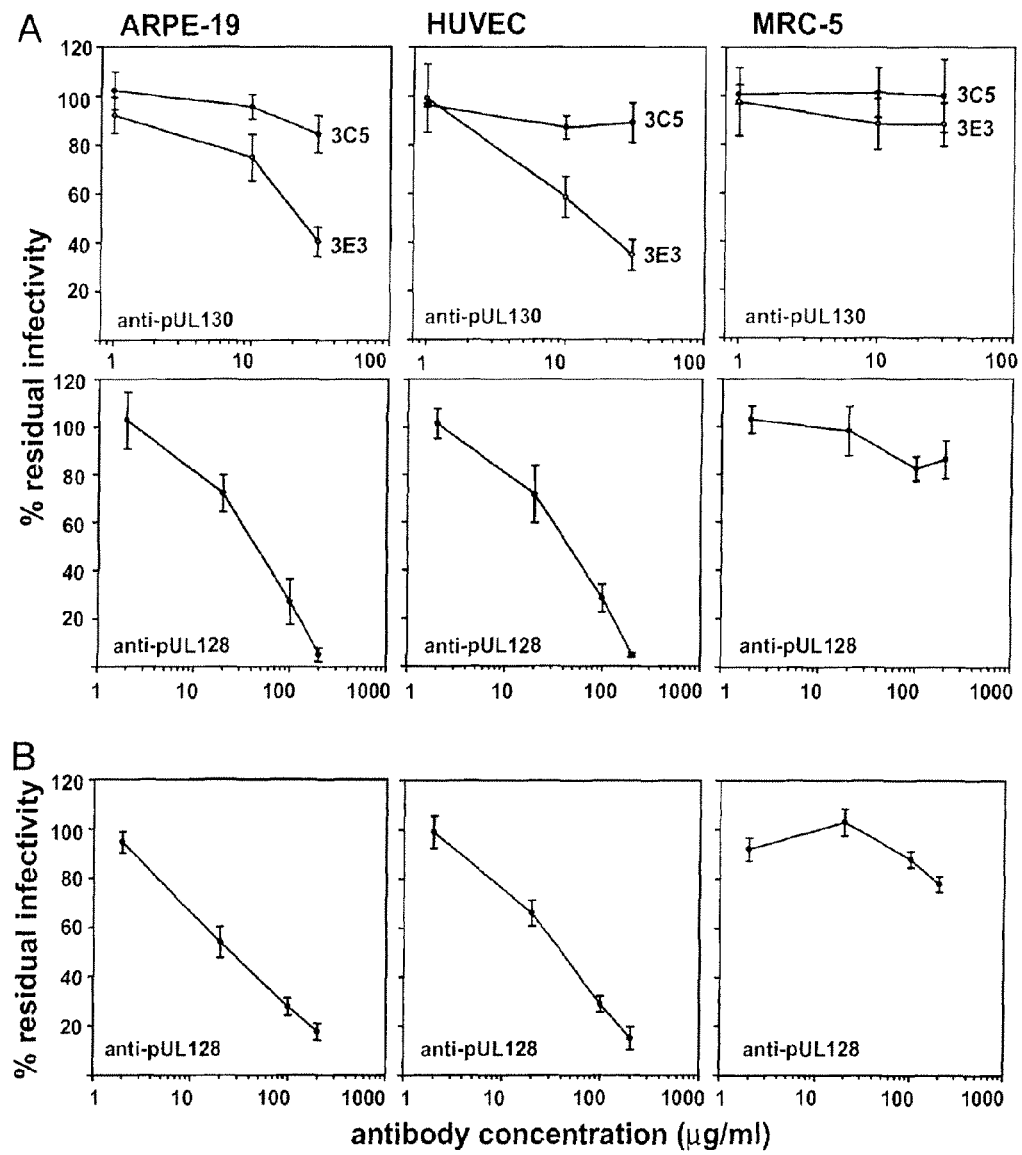
FIG. 6 shows the neutralization of human CMV infectivity in ARPE-19 epithelial cells, HUVEC endothelial cells, and MRC-5 fibroblasts. BADrUL 131 (A) or BFXwt (B) were incubated with various concentrations of anti-pUL130 3C5 or 3E3 or anti-pUL128 R551A antibodies, and residual infectivity was determined on the different cell types.

Affinity-purified antibodies were used, and no complement was added to the assays. As shown in FIG. 6A, pUL130-specific 3E3 monoclonal antibody inhibited BADrUL131 infection of ARPE-19 or HUVEC cells but not MRC-5 cells. Fifty percent neutralization was achieved at ~20 μg/ml antibody. The 3C5 antibody, which recognizes a different pUL130 epitope, did not block infection. Rabbit polyclonal antibodies to pUL128 were also observed to neutralize the ability of BADrUL131 to infect ARPE-19 and HUVEC cells, but not MRC-5 cells. The patterns of inhibition were the same for endothelial and epithelial cells, suggesting that BADrUL131 utilizes the same mechanism to infect the two cell types. The antibody to pUL128 also blocked infection of ARPE-19 and HUVEC cells by the BFXwt clinical strain of human CMV and again did not notably inhibit infection of MRC-5 cells (FIG. 6B).

EXAMPLE 3

Inhibition of Human CMV Infection of Epithelial Cells Using Anti-CD46 Antibodies An anti-CD46 antibody was purchased from a commercial source (antibody J4.48, Chemicon International). BADrUL131 is a human CMV virus that has a functional pUL128-pUL130-containing complex and can infect both fibroblasts and epithelial cells. A set amount of BADrUL131 was mixed with dilutions of the antibody to CD46, and the mixtures were used to infect ARPE-19 cells or human foreskin fibroblasts (HFF). At 24 hours after infection, cells were fixed and assayed for expression of the virus coded protein, 1E1, by immunofluorescence. This served as a measure of successful infection. The percent of positive cells were determined and used as a measure of the efficiency of infection.

Figure 7:
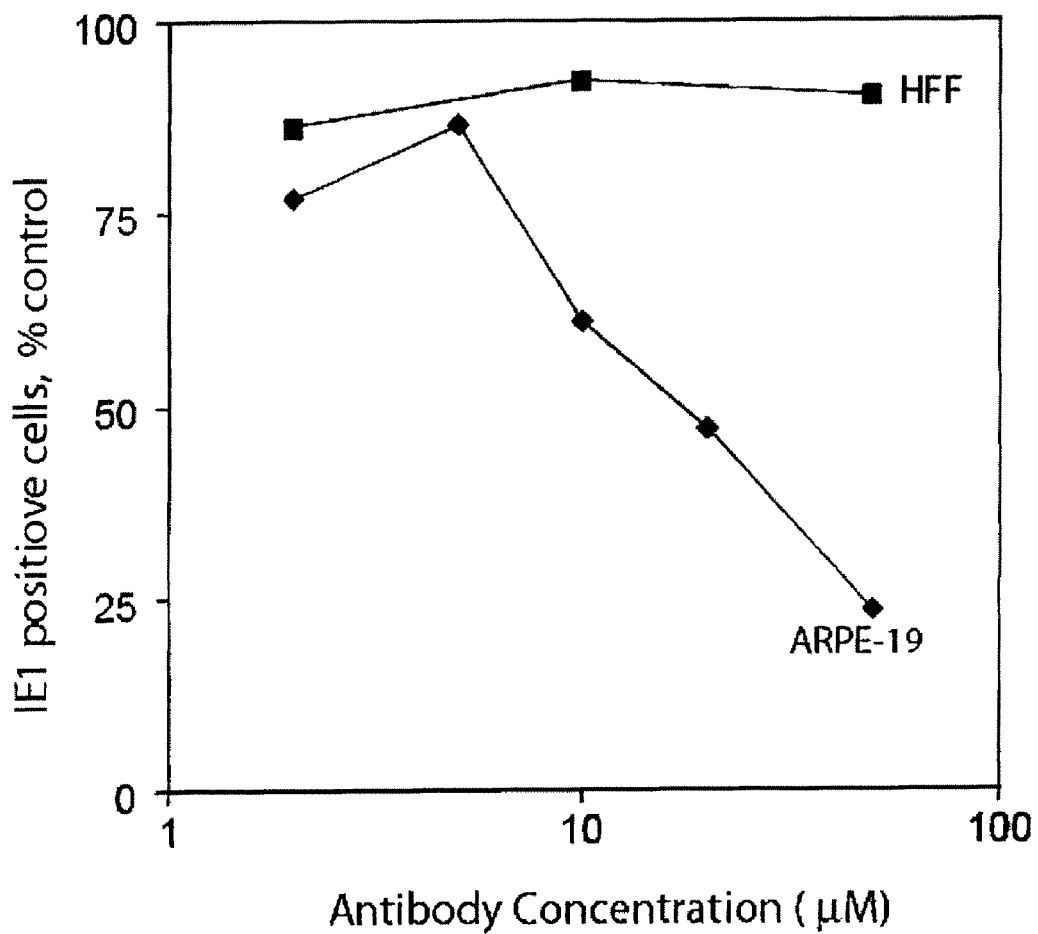
FIG. 7 shows that CD46-specific antibody significantly diminishes human CMV infection of ARPE-19 cells but not MRC-5 fibroblasts. Inhibition of infection in ARPE-19 cells increased with increasing concentrations of anti-CD46 antibody, consistent with a dose-dependent effect. Infection was monitored by quantifying the number of cells expressing the 1E1 protein encoded by human CMV.

As shown in FIG. 7, an approximately 77% inhibition of human CMV infectivity of APRE-19 epithelial cells was observed at the highest concentration of anti-CD46 antibody tested, and this amount of antibody had no effect on the ability of the virus to infect control HFF cells. This indicates that the virus utilizes CD46 to enter epithelial cells but not for entry into fibroblasts. The inhibition of infection of the ARPE-19 cells was dose-dependent, as would be expected for an antibody that inhibits infection by binding to and blocking a receptor interaction.

EXAMPLE 4

Analysis of a Mixture of Human CMV-Specific Antibodies used for Treatment of Human CMV Disease Information set forth in this example further supports the utility of human CMV UL128 and UL130 proteins (pUL128 and pUL130), and the complex with which they are associated in virus particles, for development of human CMV-specific vaccines and drugs, including antibody drugs, that prevent or treat human CMV infection. The experiments employed a commercially available antibody preparation, CYTOGAM®, which is human immune globulin containing human CMV-specific antibodies. It is employed as an intravenous therapy for prophylaxis of CMV disease associated with allogeneic transplantation. There also is evidence in the literature that administration of such antibody preparations during pregnancy is safe and there is indication that it protects against congenital infection (Nigro, G et al., 2005, N. Engl. J. Med. 353:1350-62), where approximately 1/2000 newborns suffer moderate-to-severe consequences of CMV infection.

The rationale for the experiment was as follows: if virion glycoprotein complexes containing pUL128 and/or pUL130 are important for infection of cells that are involved in human CMV pathogenesis and spread, then a human immune globulin preparation used to treat human CMV disease, i.e., CYTOGAM®, should contain antibodies to one of more components of the pUL128/pUL130 complex(es), and these antibodies should neutralize human CMV infection of cultured epithelial cells.

Figure 8:
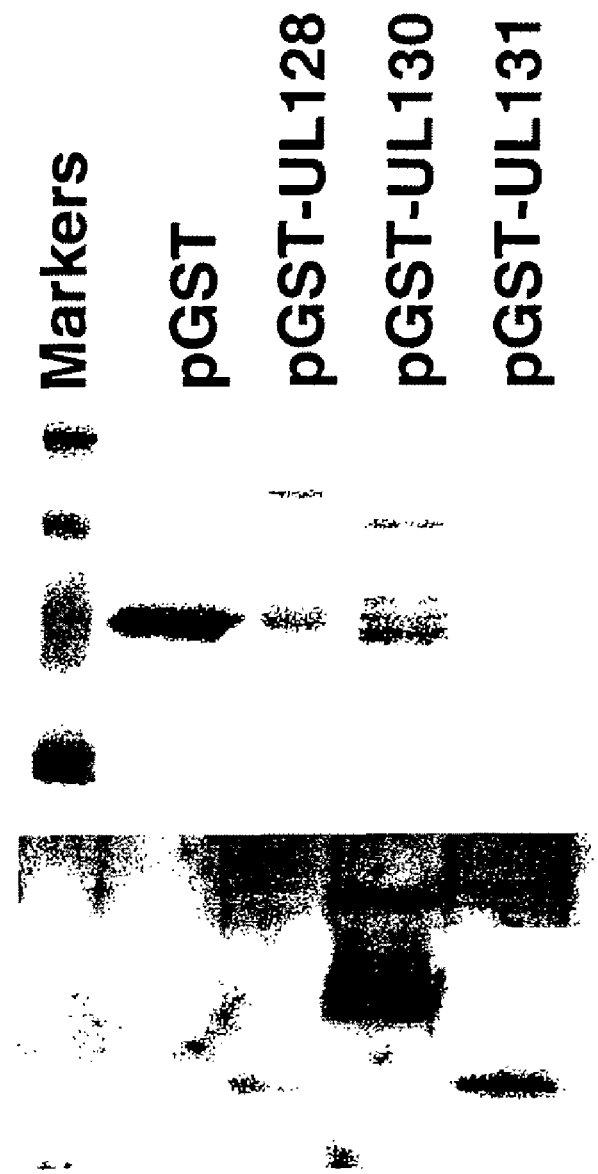
FIG. 8 shows that CYTOGAM® contains antibodies that react with UL130 protein. GST fusion proteins containing pUL128 (aa 28-171), pUL130 (aa 37-133), pUL131 (aa 28-129) or unfused GST were produce in E. coli, partially purified, resolved by electrophoresis (12% SDS-PAGE), and transferred to a nitrocellulose membrane. After blocking with skim milk, the blot was probed with a 1:5000 dilution of CYTOGAM®. The proteins reacting with CYTOGAM® were then detected by using HRP conjugated anti-human IgG and enhanced chemiluminescence. The GST fusion protein preparations include degraded species.

Initially, a western blot assay was performed to test for the presence of antibodies specific for pUL128, pUL130 and pUL131 in CYTOGAM® (FIG. 8). Partially purified glutathione-S-transferase (GST) fusion proteins were used for the analysis (FIG. 8, top panel). Whereas antibodies in CYTOGAM® did not recognize the GST fusion partner at the level of sensitivity employed in the experiment, the antibodies very strongly recognized the pUL130-containing protein and reacted to a lesser extent with pUL128 and pUL131 fusion proteins in the western blot assay (FIG. 8, bottom panel). This result indicates that CYTOGAM® contains antibodies that recognize the pUL128-pUL130-pUL131 component of the gH-gL-pUL128-pUL130-pUL131 complex in the format of a western blot assay. Further, the assay revealed that CYTOGAM® contains much more reactivity to pUL130 than to pUL128 or pUL131.

Figure 9:
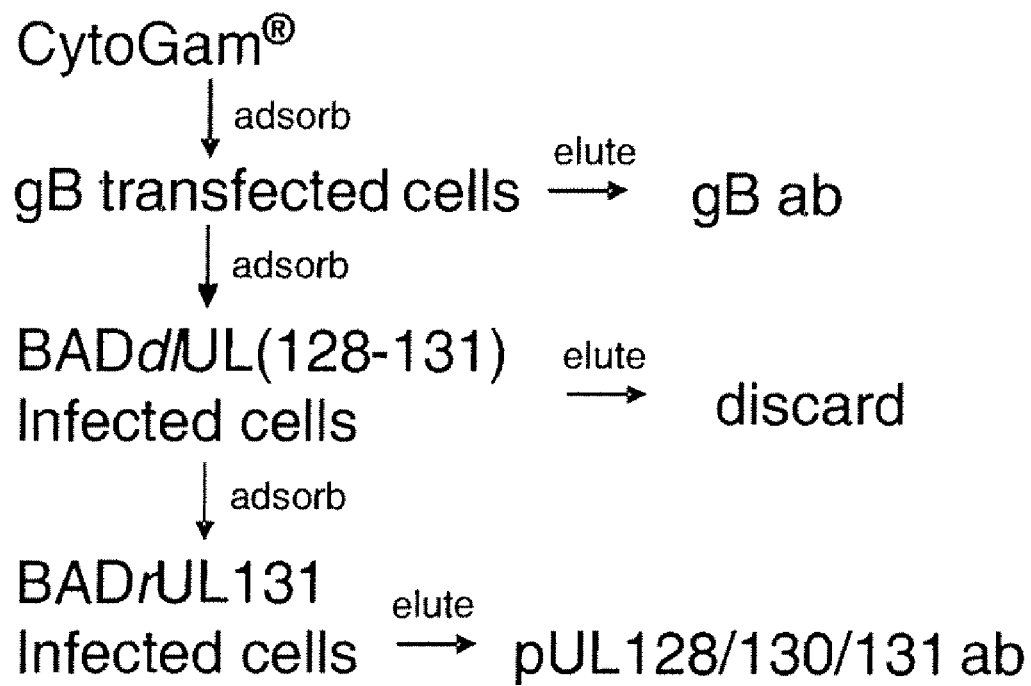
FIG. 9 shows isolation of antibody subpopulations from CYTOGAM®. MRC-5 cells were transfected with a gB expression plasmid or infected with BADdlUL(128-131) or BADrUL131 at a multiplicity of 1 pfu/cell. The cells were fixed with 4% paraformaldehyde at 72 h post transfection or infection. CYTOGAM® was diluted to 10 mg/ml and sequentially absorbed to the MRC-5 cells with each adsorption for 2 h at room temperature. After adsorption, the cells were washed three times with DPBS. Bound antibodies were eluted from plates using 0.4 M acetic acid for 5 min at room temperature, and the eluate was immediately neutralized using a saturated Tris solution to a final pH of 7.0 to 8.0. Eluted antibodies were dialyzed, concentrated in dialysis tubing by dehydration using polyethylene glycol powder, and stored at 4° C.
Figure 10:
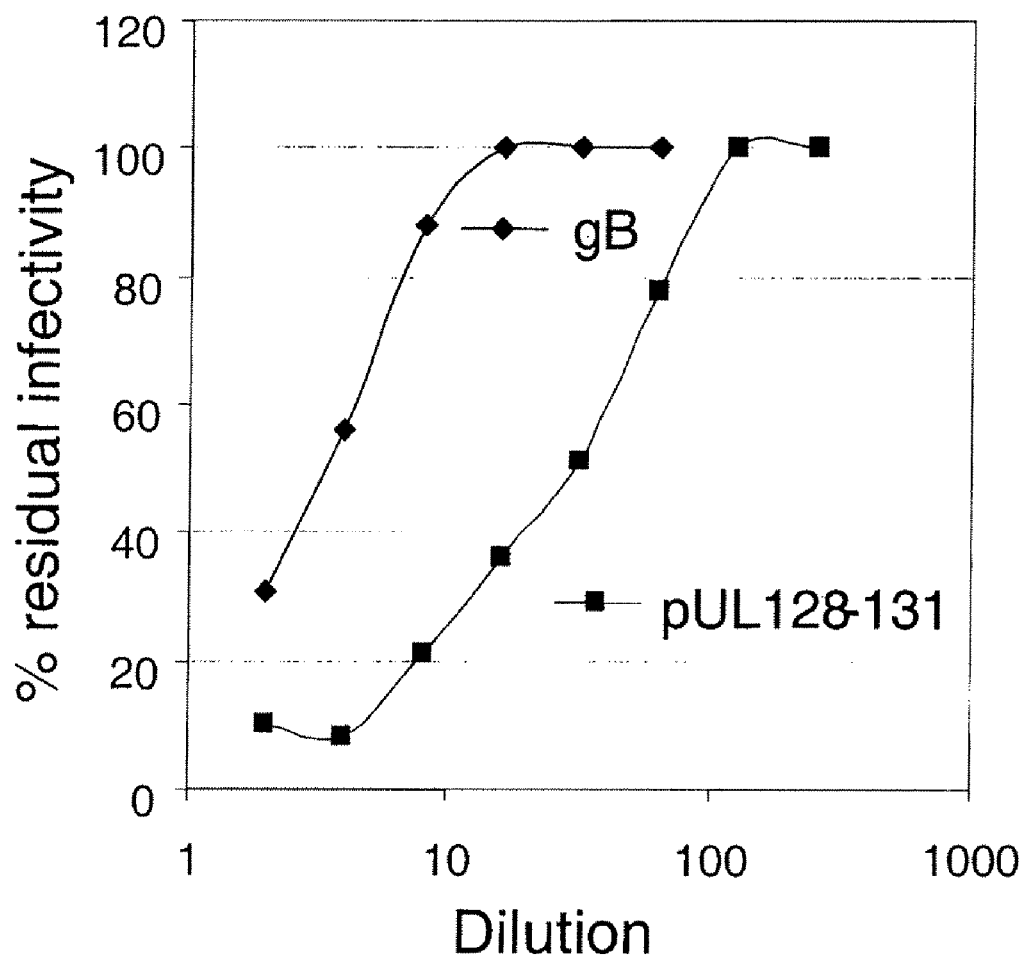
FIG. 10 shows the relative neutralizing activity of gB versus pUL128/pUL130/pUL131 antibodies isolated from CYTOGAM®. Equal amounts of gB ab or pUL128/130/131 antibody were serially diluted and incubated with ~100 pfu of BADrUL131 for 1 h at room temperature. After incubation, solutions were added to ARPE-19 epithelial cells in 96-well microtiter plates for 2 h at 37° C. All samples were tested in duplicate. After the virus solutions were removed, cells were incubated for another 20 h in fresh medium, then washed, fixed with paraformadehyde, stained with anti-IE72 monoclonal antibody 12B10 and Alexa546 conjugated anti-mouse IgG secondary antibodies. The number of fluorescence cells was compared to the number of cells infected by virus in medium lacking antibody to calculate percent residual infectivity.

Next, gB-specific and a mixture of pUL128-pUL130-pUL131-specific antibodies were isolated from CYTOGAM® (FIG. 9). Equal amounts of IgG from the two preparations were then assayed for their ability to neutralize human CMV infection of epithelial cells (FIG. 10). Results indicated that the CYTOGAM® antibodies specific for gB and for pUL128-pUL130-pUL131 are both able to neutralize human CMV infectivity. It also suggests that at the same concentration, the partially purified pUL128/pUL130/pUL131 antibody has more neutralizing activity than the partially purified gB antibody from CYTOGAM®.

To summarize, CYTOGAM® is known to contain a mixture of human CMV-specific antibodies used for treatment of human CMV disease. We have demonstrated that CYTOGAM® contains antibodies against the pUL128-pUL130-pUL131 complex, and these antibodies are able to neutralize the infectivity of human CMV. Indeed, it appears that pUL128-pUL130-pUL131 antibody was more potent in the neutralizing assay than gB antibody from CYTOGAM®. These results have implications for anti-human CMV therapy. For instance, an antibody or mixture of antibodies that bind to pUL128-pUL130-pUL131 should be useful for treatment of human CMV disease. Further, pUL 130 appears to be a principal target and likely the major target within the pUL128-pUL130-pUL131 complex that is recognized by CYTOGAM®. Accordingly, an antibody or antibodies to pUL130 alone or in combination with antibodies to other glycoproteins may be able to substitute for CYTOGAM®. The observations with CYTOGAM® further substantiate the utility of the pUL128-pUL130-pUL131 complex and its individual components as antigens for immunization. Since CYTOGAM® contains immune globulin from pooled human donors and since it contains predominant reactivity to the pUL130 subunit of the pUL128-pUL130-pUL131 complex, pUL130 alone or in combination with other glycoproteins should serve as an effective anti-human CMV subunit vaccine.

The present invention is not limited to the embodiments described and exemplified above, but is capable of variation and modification within the scope of the appended claims.

What is claimed is:

1. A method to induce an immune response against cytomegalovirus (CMV) in a mammal, comprising the step of administering an immunogenic composition comprising a pharmaceutically acceptable carrier and a complex of CMV proteins comprising pUL128 and at least one of pUL130, pUL131, gH, gL or gB, or pUL130 and at least one of pUL128, pUL131, gH, gL or gB, wherein the immunogenic composition induces production of antibodies against CMV that treat CMV infection of endothelial cells and/or epithelial cells.

2. The method of claim 1, wherein two or more of pUL128, pUL130, pUL131, gH, gL or gB are linked into one polypeptide chain.

3. A method of treating cytomegalovirus (CMV) infection comprising the step of administering a therapeutically effective amount of a composition comprising a pharmaceutically acceptable carrier and a complex CMV proteins comprising pUL128 and at least one of pUL130, pUL131, gH, gL or gB, or pUL130 and at least one of pUL128, pUL131, gH, gL or gB, wherein the immunogenic composition induces production of antibodies against CMV that treat CMV infection of endothelial cells and/or epithelial cells.

4. The method of claim 3, wherein the at least one CMV protein or complex is coupled to a carrier protein.

5. The method of claim 4, wherein the carrier protein is albumin, ovalbumin, *Pseudomonas* endotoxin, tetanus toxin, ricin toxin, diphtheria toxin, cholera toxin, heat labile enterotoxin, keyhole limpet hemocyanin, epidermal growth factor, fibroblast growth factor, transferrin, platelet derived growth factor, poly-L-lysine, poly-L-glutamine, or mannose-6-phosphate.

6. The method of claim 1 or 3, wherein the complex comprises pUL128 and pUL130.

7. The method of claim 1 or 3, wherein the complex comprises pUL128 and gH.

8. The method of claim 1 or 3, wherein the complex comprises pUL130 and gH.

9. The method of claim 1 or 3, wherein the complex comprises pUL128, pUL130 and gH.

10. The method of claim 1 or 3, wherein the complex comprises pUL128, gH and gL.

11. The method of claim 1 or 3, wherein the complex comprises pUL130, gH and gL.

12. The method of claim 1 or 3, wherein the complex comprises pUL128, pUL130, gH and gL.

* * * * *